United States Patent [19]
Tolstoshev et al.

[11] Patent Number: 5,824,505
[45] Date of Patent: Oct. 20, 1998

[54] VECTORS, TRANSFORMED CELLS AND PROCESS FOR THE PREPARATION OF HIRUDIN

[75] Inventors: Paul Tolstoshev, Mundelsheim; Richard Harvey; Michael Courtney, both of Strasbourg; Jean-Pierre LeCocq, Reichsteet, all of France

[73] Assignee: Transgene S.A., Paris, France

[21] Appl. No.: 500,111

[22] Filed: Jul. 10, 1995

Related U.S. Application Data

[63] Continuation of Ser. No. 312,972, Sep. 30, 1994, abandoned, which is a continuation of Ser. No. 159,697, Dec. 1, 1993, abandoned, which is a continuation of Ser. No. 26,220, Mar. 1, 1993, abandoned, which is a continuation of Ser. No. 793,287, Nov. 13, 1991, abandoned, which is a continuation of Ser. No. 554,076, Jul. 16, 1990, abandoned, which is a continuation of Ser. No. 432,318, Nov. 3, 1989, abandoned, which is a continuation of Ser. No. 808,447, Nov. 25, 1985, abandoned.

[30] Foreign Application Priority Data

| Mar. 27, 1984 | [FR] | France | 84 04755 |
| Aug. 27, 1984 | [FR] | France | 84 13250 |
| Mar. 27, 1985 | [WO] | WIPO | PCT/FR85/00062 |

[51] Int. Cl.$^6$ ............................. C12P 21/02; C12N 15/63; C12N 1/21
[52] U.S. Cl. ................... 435/69.2; 435/320.1; 435/252.3; 435/252.33
[58] Field of Search ............................. 435/320.1, 252.3, 435/252.33, 69.2

[56] References Cited

U.S. PATENT DOCUMENTS

| 4,517,294 | 5/1985 | Bock et al. | 435/69.4 |
| 4,578,355 | 3/1986 | Rosenberg | 435/320.1 |
| 5,232,912 | 8/1993 | Krstenansky | 514/15 |
| 5,422,249 | 6/1995 | Liersch et al. | 435/69.2 |
| 5,516,656 | 5/1996 | Misawa et al. | 435/69.2 |
| 5,573,929 | 11/1996 | Misawa et al. | 435/69.1 |

FOREIGN PATENT DOCUMENTS

| 0094887 | 11/1983 | European Pat. Off. | C12N 15/00 |
| 94887 | 11/1983 | European Pat. Off. | |

OTHER PUBLICATIONS

Dodt et al. FEBS 165:180–84, 1984 (Jan.).
Bagdy et al. In. Methods in Enzymology, vol. XLV, pp. 669–678, 1976, Academic Press, NY.
Chemical Abstracts, vol. 100, No. 152937g "The complete amino acid sequence of hirudin, a thrombin specific inhibitor. Application of color carboxymethylation." J. Dodt et al. FEBS Lett. (1984) 165(2):180–184.
"Plasmid vectors for positive selection of DNA inserts controlled by the pL promoter, repressor and antitermination function", by A. Honigman and A.B. Oppenheim, Gene, vol. 13, 1981, pp. 289–298.
Chemical Abstracts, vol. 100, No. 152937g "The complete amino acid sequence of hirudin, a thrombin specific inhibitor. Application of color carboxy–methylation." J. Dodt et al. FEBS Lett. (1984) 165(2):180–184.
"Plasmid vectors for positive selection of DNA inserts controlled by the pL promoter, repressor and antiterminatin function", by A. Honigman and A.B. Oppenheim, Gene, vol. 13, 1981, pp. 289–298.
Dodt et al. FEBS 165:180–84, 1984 (Jan.).
Bagdy et al. In. *Methods in Enzymology*, vol. XLV, pp. 669–678, 1976., Academic Press, NY.

Primary Examiner—Robert A. Wax
Assistant Examiner—Kawai Lau
Attorney, Agent, or Firm—Burns, Doane, Swecker & Mathis, L.L.P.

[57] ABSTRACT

The present invention relates to vectors for cloning, in a host cell, hirudin or an analog of hirudin, characterized in that it comprises the gene for encoding hirudin or an analog of hirudin, and the elements for the expression of this gene in said host cell, said coding gene beginning, after the starting sequence, by an Ile codon and a Thr codon. This invention also relates to the process for the preparation of hirudin or analogs of hirudin as well as the hirudin or anologs of hirudin obtained.

8 Claims, 25 Drawing Sheets val-val-tyr-thr-asp-cys-thr-glu-ser-gly-gln-asn-leu-cys-leu-cys-glu-gly-ser-asn-
val-cys-gly-gln-gly-asn-lys-cys-ile-leu-gly-ser-asp-gly-lys-asn-gln-cys-val-
thr-gly-glu-gly-thr-pro-lys-pro-gln-ser-his-asn-asp-gly-asp-phe-glu-glu-ile-pro-
glu-glu-tyr-leu-gln
         |
        SO₃H

FIG. 1

(a) COOH - - - glnprolysprothrglyglugythrvalcysglnasnlysglugly - - - NH₂

(b) 5' CTGAGGCTTAGGAGTACCCTGGCCGGTGACGCACTGGTTCTTCTCGCC 3'

(c) 3' AAGTCCGAAGCCACATGGAAGCGGTCACTGTGTAACCAGGGGGGGGG 5'  | polyG (d) COOH - - - glu prolysprothrglygluglythrvalcysgln

FIG. 2

GCA ATC TGC GTG TCT CAA GCA ATT ACT TAC ACT GAT TGT ACA GAA TCG GGT CAA AAT TTG TGC CTC TGC GAG GGA AGC AAT GTT TGC GGT
Ala Ile Cys Val Ser Gln Ala Ile Thr Tyr Thr Asp Cys Thr Glu Ser Gly Gln Asn Leu Cys Leu Cys Glu Gly Ser Asn Val Cys Gly

AAA GGC AAT AAG TGC ATA TTG GGT TCT AAT GGA AAG GGC AAC CAA TGT GTC ACT GGC GAA GGT GAA CCG ACA AAC CCT GAA AGC CAT AAT AAC
Lys Gly Asn Lys Cys Ile Leu Gly Ser Asn Gly Lys Gly Asn Gln Cys Val Thr Gly Glu Gly Glu Pro Thr Asn Pro Glu Ser His Asn Asn

GGC GAT TTC GAA GAA ATT CCA GAA GAA TAT TTA CAA TAT CAA GAA ATG AAA TGA AAA GAA TAT CAA TCA TAG AGA ATT TAA AAA CAT TTC CAT
Gly Asp Phe Glu Glu Ile Pro Glu Glu Tyr Leu Gln Tyr Gln Glu Met Lys ···

AGCTAAGCTATTTACCAATAAATAAATTAATTTTTCCATTGAATCTCAATCATATTCAGCTATTTACCAATAAATAAATTAATTTTCCATGA

FIG. 3

CONSTRUCTION PTG941

PTG941

IFN

PTG909                    *MetCys Tyr Cys GlnAspPro Tyr*
TAAGGAAGTACTTA<u>CATATG</u>TGTTATTGCCAGGACCC<u>ATATG</u>....
                     NDE I                              NDE I

NDE I
+
TATGTGCTACTGTCAGGATCCC
  ACACGATGACAGTCCTAGGGAT

IFN

PTG941                  *MetCys Tyr Cys GlnAspProTyr*
TAAGGAAGTACTTA<u>CATATG</u>TGCTACTGTCAG<u>GATCCC</u>TAT
                     NDE I                     BAMHI

FIG. 14

CONSTRUCTION PTG951
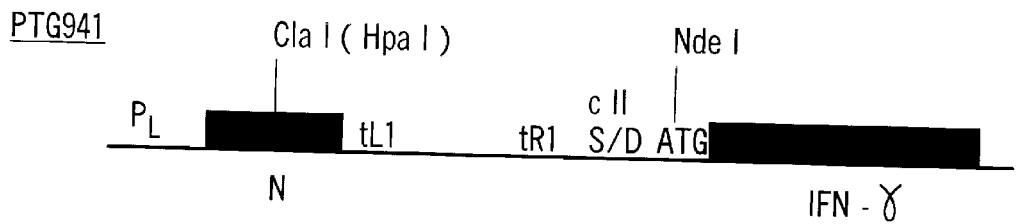
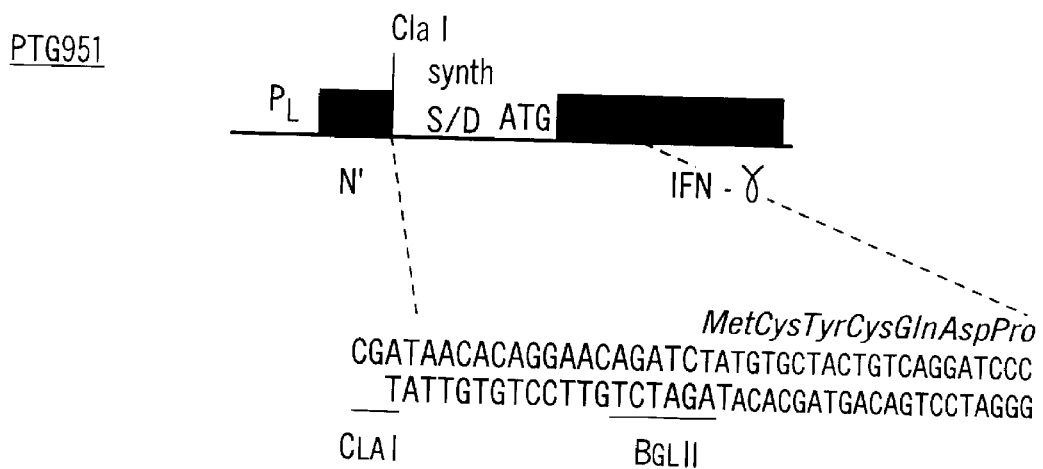
FIG. 15

FIG. 18

```
                                    Pst I
                                     ↓  1                                    21
                             a)  (G)nGCA ATC TGC GTG TCT CAA GCA
                             b)      Ala Ile Cys Val Ser Gln Ala 22                                                                  66
a)      ATT ACT TAC ACT GAT TGT ACA GAA TCG GGT CAA AAT TTG TGC CTC
         1                                                                   15
b)      Ala Ile Cys Val Ser Gln Ala Glu Ser Gly Gln Asn Leu Cys Leu
         1   2
c)      Val Val ---------------------------------------------------

67                                                                  111
        TGC GAG GGA AGC AAT GTT TGC GGT AAA GGC AAT AAG TGC ATA TTG
         16                                                                  30
        Cys Glu Gly Ser Asn Val Cys Gly Lys Gly Asn Lys Cys Ile Leu
                                         24
        -------------------------------- Gln ---------------------

112                                                                 156
        GGT TCT AAT GGA AAG GGC AAC CAA TGT GTC ACT GGC GAA GGT ACA
         31                                                                  45
        Gly Ser Asn Gly Lys Gly Asn Gln Cys Val Thr Gly Glu Gly Thr
             33      35  36
        ---- Asp ---- Glu Lys ------------------------------------
                                                    Taq I
                                                     ↓
         157                                                                 201
        CCG AAC CCT GAA AGC CAT AAT AAC GGC GAT TTC GAA GAA ATT CCA
         46                                                                  60
        Pro Asn Pro Glu Ser His Asn Asn Gly Asp Phe Glu Glu Ile Pro
             47      49          53
        --- Lys ---- Gln ---------Asp-----------------------------
                                                                      Aha III
         202                                                           256 ↓
        GAA GAA TAT TTA CAA TGAAAAATGAAAGAATATCAATCATAGAGAATTTTGATTT
         61              65
        Glu Glu Tyr Leu Gln

------------------

257                                                                 316
          AAAAACATTTCCATAGCTAAGCTATTTACCAATAAATAAATTAATTTTTCCATTGAATCT 317                                                                 376
          CAATCATATTTACTCTCAATCATATTCAGCTATTTACCAATAAATAAATTAATTTTTCCA

Pst I
               ↓
         377
          TGA(C)n
```

```
Eco RI    10     1      20        ▼30        40    2      50
 ┌AATTCAACAT ATGGTAGTTT ATACCGACTG CACCGAATCC GGTCAGAACC
 └GTTGTA    TACCATCAAA TATGGCTGAC GTGGCTTAGG CCAGTCTTGG
                               5              ▲               6

▼      60     3      70    ▼80          90    4      100
TGTGCCTGTG CGAAGGTTCT AACGTTTGCG GTCAGGGTAA CAAATGCATC
ACACGGACAC GCTTCCAAGA TTGCAAACGC CAGTCCCATT GTTTACGTAG
                 ▲                   7                        ▲              8
Bam HI                       130
  ▼    110       9    120     ▼           140   10     150
CTCG┌GATCCG ACGGTGAAAA AAACCAGTGC GTTACAGGTG AAGGTACTCC
GAGCCTA└GGC TGCCACTTTT TTTGGTCACG CAATGTCCAC TTCCATGAGG
         ▲                              12                  ▲

▼     160     11    170         180          190          200
GAAACCGCAG TCTCATAACG ACGGTGACTT┌
CTTTGGCGTC AGAGTATTGC TGCCACTGAA└GC┐
   13              ▲                 14       Taq I
```

Oligonucleotides

| | 1 | | | 2 |
|---|---|---|---|---|
| 1 | 27 bases | | 9 | 25 |
| 2 | 25 | | 10 | 25 |
| 3 | 25 | | 11 | 26 |
| 4 | 27 | | 12 | 30 |
| 5 | 32 | | 13 | 25 |
| 6 | 25 | | 14 | 19 |
| 7 | 25 | | | |
| 8 | 22 | | | |

FIG. 23

VECTORS, TRANSFORMED CELLS AND PROCESS FOR THE PREPARATION OF HIRUDIN

This application is a continuation, of application Ser. No. 08/312,972, filed Sep. 30, 1994, which is a continuation of application Ser. No. 08/159,697, filed Dec. 1, 1993, which is a continuation of application Ser. No. 08/026,220, filed Mar. 1, 1993; which is a continuation of application Ser. No. 07/793,287, filed Nov. 13, 1991; which is a continuation of application Ser. No. 07/554,076, filed Jul. 16, 1990; which is a continuation of application Ser. No. 07/432,318, filed Nov. 3, 1989; which is a continuation of application Ser. No. 06/808,447, filed Nov. 25, 1985, all now abandoned.

The present invention relates to vectors for the cloning and expression of the DNA sequence coding for hirudin or hirudin analogs, microorganisms transformed by these vectors and processes which enable hirudin to be obtained by fermentation, as well as the hirudin obtained.

The anticoagulant activity present in the salivary glands of the medicinal leeches *Hirudo medicinalis* originates from a small polypeptide known as hirudin. This very specific and very effective thrombin inhibitor has been widely studied recently, since it potentially represents a very useful therapeutic agent. However, the extreme difficulty and cost in isolating and purifying it has prevented it from being used more widely, or even from being studied at the clinical level. The cost of the material is on the order of 1,300 to 1,600 francs (1983) for 2,000 U.

The present invention relates to a means for producing hirudin by cloning the genes and the expression thereof by means of the recombinant DNA technique in a heterologous host cell, in order to obtain a large amount of polypeptide having the biological properties of hirudin.

The polypeptide with anti-thrombin activity obtained from the salivary glands of leeches was isolated for the first time in the middle of 1950 (1, 2). This protein, known as hirudin, was purified approximately 650 times, starting from the heads of leeches, to obtain a specific activity of 8,500 units per milligram.

The molecular weight of the protein was then estimated at approximately 16,000. This protein was stable to denaturation by heat and had an isoelectric point of 4.8. In electrophoresis on paper, the purified product migrates in the form of a single band and amino acid analysis shows that the material is very rich in acidic amino acids, aspartic acid and glutamic acid.

Further stages of purification (3) increase the specific activity to 10,400 U/mg, and isoleucine was identified as the N-terminal amino acid (3, 4).

It was possible to demonstrate that hirudin activity resisted digestion with the proteolytic enzymes plasmin, chymotrypsin A and trypsin, but was sensitive to digestion with papain, pepsin and subtilopeptidase A (3).

The estimated molecular weight is now slightly less than it was in the initial papers, and this molecular weight is regarded as being of the order of 10,000 daltons. The first estimate of the dissociation constant of the 1:1 thrombin-hirudin complex ($0.8 \times 10^{-10}$) indicates an extremely strong association between these two molecules (5). For practical reasons, the non-covalent complex between these two molecules can be regarded as non-dissociable in vivo.

The mechanism of action of hirudin as an anticoagulant is only just beginning to be understood (5). The substrate for the binding of hirudin is thrombin, which is a proteolytic enzyme which, through activation (by means of the activated factor X) from its zymogen form, prothrombin, cleaves the fibrinogen in the circulatory stream to convert it to fibrin, which is required for the formation of the blood clot.

Hirudin is a very specific thrombin inhibitor, which reacts more rapidly with thrombin than fibrinogen does. Furthermore, it is not necessary to have other clotting factors or other plasma constituents present. The interaction between the two molecules is at least partially due to their ionic interaction, since acetylation of the free amino groups of thrombin produces a loss in the binding of hirudin. Furthermore, hirudin binds in the same sites as those occupied by the fibrinopeptide and not on the active sites of the thrombin, since acetylated thrombin retains its esterase activity which is not inhibited by hirudin, and since thrombin treated with DFP (diisopropyl fluorophosphate), which phosphorylates the serine-active centers in thrombin, continues to bind hirudin.

The next development in the study of hirudin consisted of the development of a process for extracting hirudin from whole leeches (16) instead of the very awkward process which consisted in dissecting the head of the animal. The final product obtained by this process has a biological activity similar to that of the hirudin obtained from the heads, but has a specific activity of 6,500 antithrombin units per milligram.

The estimated size of this compound, determined by equilibrium sedimentation, is 12,000, but the important difference between this preparation and the preceding preparations is that valine was identified as the N-terminal amino acid instead of isoleucine, which had originally been found. The cause of this difference was apparently explained when it was demonstrated that the second component of the N-terminal end turned out to be valine, and since the dansyl dipeptide val—val is resistant to acid hydrolysis, it was at first thought (7) that the initial N-terminal end with a val-val dipeptide had been confused with the isoleucine derivative, since these components are not well resolved by the chromatographic separation used.

A preparation of hirudin from the whole animal was used to determine the amino acid sequence of the protein (8, 9) which is shown in FIG. 1. There appears to be no carbohydrate attached to hirudin, but the tyrosine residue at position 63 is modified by an O-sulfate ester group.

The function of this modification is unknown, but it is significant that a similar modification also occurs in the fibrinopeptide B of a large number of animal species (9).

A recent study (10) has demonstrated that, when the sulfate ester is made to disappear completely, the activity is reduced to only 55% of the initial hirudin activity.

The question regarding the nature of the N-terminal end of hirudin has coming up again in studies (12, 13) which appear to indicate that there are two different forms of hirudin; one form having low activity, known as pseudo-hirudin, which is thought to have been extracted from the bodies of leeches, with the val—val sequence at the N-terminal end; and a form which predominates in the heads, which appears to be highly active and to have an isoleucine radical at its N-terminal end.

The specific and very substantial antithrombin activity of hirudin immediately suggests a clinical application, that is to say, its application as an anticoagulant.

Hirudin has been the subject of much study in animals for its anticoagulant properties. The most detailed study (14) describes the activity of hirudin in the prevention of venous thromboses, vascular occlusions and disseminated intravascular coagulations (DIC) in rats. Hirudin is well tolerated by rats, dogs, rabbits and mice when it is in a highly purified form and is injected intravenously. The $LD_{50}$ in mice is greater, 500,000 U/kg of body weight (that is to say, 60 mg/kg). Another study (15) shows that mice tolerate doses ranging up to 1 g per kg and that rabbits tolerate up to 10 mg/kg both intravenously and subcutaneously. In mice, repeated injections over a period of two weeks do not lead to sensitization reactions. Two other independent studies, one using dogs (16) and the other (17) demonstrating the activity of hirudin in the prevention of DIC in rats, concur with the positive results of Markwardt and his co-workers.

It has also been possible to demonstrate that hirudin counteracts the endotoxins induced by DIC in pigs, and thus constitutes a potential solution to the very serious problems caused by endotoxinemias which lead to high mortality in pigs. Furthermore, hirudin in experimental animals is rapidly eliminated (it has a half-life on the order of 1 hour) in a still biologically active form, by way of the kidneys.

This study suggests that hirudin can constitute a useful clinical agent as an anticoagulant. Furthermore, the prephase of blood coagulation is not affected in view of the high specificity of the action of hirudin. The antithrombin activity is dependent on the dose, and the effect of hirudin is rapidly reversible in view of its rapid renal elimination. It has been possible to demonstrate that hirudin is far superior to heparin for treating DIC (14, 17), as could be expected in view of the fact that DIC is accompanied by a decrease in antithrombin III (a cofactor required for the action of heparin) and a salting-out of platelet factor 4, which is a very effective anti-heparin agent.

One of the studies has demonstrated the possibility that hirudin may be absorbed by the skin of humans (19), although the results obtained remain somewhat difficult to interpret.

Commercial preparations of crude leech extracts are available (Hirucreme, Exhirud-Blutgel), but further tests with larger doses of a highly purified material are needed to establish whether this is a useful administration route.

In general, the preferred administration routes are the intravenous, intramuscular and percutaneous routes. Other administration routes have been reported for hirudin, in particular, the oral route (BSM 3,792M).

In combination with other components, this product can also be used in the treatment of psoriasis and other cutaneous disorders of the same type, as described in DOS 2,101,393.

Hirudin can, in addition, be used as an anticoagulant in clinical tests in the laboratory, and a research tool. In this case, the high specificity for a single stage in the coagulation of the blood can have a substantial advantage over the anticoagulants which are commonly used and which are much less specific in their action.

Furthermore, hirudin can be very useful as an anticoagulant agent in extracorporeal circuits and in dialysis systems, where it can have substantial advantages over other anticoagulants, especially if it can be immobilized in an active form on the surface of these artificial circulatory systems.

Finally, the use of labeled hirudin can constitute a simple and effective method for measuring the levels of thrombin and prothrombin.

In summary, hirudin has a large number of possible applications:
1) as an anticoagulant in critical thrombotic conditions, for the prophylaxis and prevention of extension of the existing thromboses;
2) as an anticoagulant for reducing hematomas and swellings after microsurgery, since substantial use is made of living leeches;
3) as an anticoagulant in extracorporeal circulation systems and as an anticoagulant agent for coating synthetic biomaterials;
4) as an anticoagulant in clinical tests on blood samples in laboratory experiments;
5) as an anticoagulant in clinical research on coagulation and as an experimental tool;
6) as a possible topical agent for cutaneous application in the treatment of hemorrhoids, varicose veins and edema; and
7) as a component in the treatment of psoriasis and other related disorders.

Finally, hirudin can be used to bind thrombin in media in which thrombin causes interference (an assay, an experiment or treated blood, for example). In particular, hirudin permits coagulation to be limited in extracorporeal circuits.

Labeled hirudin can, in addition, be used to detect clot formation. In effect, clot formation demands the conversion of circulating prothrombin to thrombin, to which the hirudin becomes selectively bound. The detection of an accumulation of labeled hirudin at a point in the patient's body permits the formation of a clot to be visualized.

Despite these many advantages as an anticoagulant, hirudin has not hitherto been used, widely even in clinical research. This is due to the fact that the natural material is very difficult to obtain in pure form, and above all, that it is particularly expensive to even begin clinical trials in order to demonstrate a potential use. Although there are adequate purification processes (20, 21) for obtaining very pure samples, the difficulty of obtaining the basic material (leeches) in sufficient amount remains the major obstacle.

Although hirudin is sold commercially by various companies (Sigma, Plantorgan, Pentopharm), such preparations show an activity which can vary enormously, and are highly variable in their purity.

For this reason, the production of hirudin by recombinant DNA technology is an especially attractive solution for obtaining this material in large quantities and at reasonable cost, in order to permit this type of product to be tested and used.

In the discussion which follows, the term "hirudin" will, for the most part, be used. However, it will be understood from the above and from additional factors which emerged from the present study, that there are several forms of hirudin, and consequently, the term "a hirudin" would be the more correct term.

For this reason, in the discussion which follows, it will be understood that the term "hirudin" refers to any one of the forms of natural or synthetic hirudin, that is to say, a product having the same activity in vivo as hirudin, which will sometimes be referred to as a "hirudin analog".

It is, moreover, appropriate to note that the products referred to as "hirudin analogs", obtained from bacteria, are devoid of the O-sulfate ester function but that, on the other hand, "bacterial hirudin may contain at the N-terminal end a methionine amino acid which does not appear in the native hirudin. But it is clear that, the term "hirudin analog" also refers to protected products of biological origin which have been modified after they have been produced, in particular, by chemical reaction or enzymic reaction.

The present invention relates to new vectors for the cloning and expression of hirudin or a hirudin analog in a host cell, which vectors contain the gene coding for hirudin or a hirudin analog and the elements for expression of this gene in the host cell.

The nature of the expression elements can vary depending on the nature of the host cell. Thus, in bacterial cells, the expression elements will contain at least one bacterial promoter and a ribosome binding site (which constitutes that which will sometimes be referred to as the coding region for the initiation of translation).

In general, the vectors according to the present invention will contain, in addition to the gene coding for hirudin, the following:

the origin of replication of a bacterial plasmid, a promoter, especially all or part of a bacteriophage λ promoter, i.e., $P_L$, $P_R$ or $P'_R$;

a region coding for the initiation of translation, incorporating the ATG either on the 5' end of the hirudin gene, or on the 5' end of the hirudin gene fused on the 5' side with another protein; this fusion is to make it possible to express a protein of high molecular weight which is degraded to a smaller extent in E. coli.

The presence of an origin of replication for a plasmid is essential to enable the vector to replicate in corresponding bacterial cells. In the case of E. coli, the origin of replication of plasmid pBR322 will preferably be used. Plasmid pBR322 has, in effect, the advantage of providing a high copy number, and thus, increases the quantity of plasmids producing the desired protein.

Among the bacteriophage λ promoters, the main leftward promoter, designated λ $P_L$, will preferably be used. $P_L$ is a powerful promoter responsible for the early transcription of λ.

It is also possible to use other bacteriophage λ promoters, in particular, the rightward promoter $P_R$ or the second rightward promoter $P'_R$.

Although it is possible to use very varied translation initiation sequences, it is preferable to use all or part of the ribosome binding site of the bacteriophage λ protein cII, hereinafter referred to as λ cIIrbs.

As will be shown below, it is also possible to use synthetic sequences, in particular, all or part of the sequence:
ATAACACAGGAACAGATCTATG.

The vector in question preferably contains, in addition, a transcription antitermination function encoded, eg., by the N gene of λ, referred to as λ N. In the presence of the gene N transcription product, transcription starting from $P_L$ continues beyond most of the stop signals.

This avoids the problems which are caused by a premature stopping of transcription, which can occur when the cloned foreign genes possess such stop signals. In addition, it has been shown that expression starting from $P_L$ is improved in an $N^+$ environment.

In order to avoid the problems of toxicity and instability in the host/vector system when continuous producing large amounts of a foreign protein, it is necessary to provide for the control of the activity of the promoter by adjoining thereto all or part of an inducible expression system, in particular, a temperature inducible system.

Control by temperature of the synthesis of the foreign protein is preferably accomplished at the level of transcription, by means of a temperature sensitive repressor encoded in the host bacterium, for example cI857, which represses $P_L$ activity at 28° C. but is inactivated at 42° C. The repressor acts on the operator $O_L$ which is adjacent to the promoter $P_L$. Although in the above case a proportion of the temperature inducible expression system is an integral part of the host bacterium, it is possible to provide for this system to form part of the vector itself.

The vector in question can also contain a gene for resistance to an antibiotic, for example ampicillin in the case of pBR322, but other resistance genes can be used for resistance to tetracycline ($Tet^r$) or chloramphenicol ($Cm^r$).

The incorporation of such a marker is necessary for the selection of the bacteria containing the transformants carrying the plasmid according to the invention during the cloning experiments.

The incorporation of a resistance gene permit the stability of the plasmid to be increased by imposing a selection pressure during fermentation, and furthermore, facilitates the isolation of the transformants.

For cloning, it is advantageous to have available a system whereby the insertion of a foreign DNA into a plasmid can be detected.

By way of example, it is possible to provide in the cloning zone the N-terminal fragment of E. coli, β-galactosidase (lacZ'), by fusing this with the translation initiation region derived from λ cII. This and this places the translation of the α fragment under the control of the cII sequences.

The α fragment is complemented by the expression of the C-terminal ω fragment encoded in the host, and this leads to β-galactosidase activity in the cells. This β-galactosidase activity produces blue colonies in the presence of a chromophoric substrate, 5-bromo-4-chloro-3-indolyl-D-galactosidase (sic).

At 28° C., the $P_L$ promoter is inactivated, the α fragment is not synthesized and the colonies remain colorless. When the temperature is raised to 42° C., the $P_L$ promoter is activated, the α fragment is synthesized and the colonies turn blue.

The insertion of foreign DNA into the cloning sites located in this detection system prevents the synthesis of the β-galactosidase and hence leads to color-less colonies both at 28° C. and at 42° C. It is also possible to replace the lacZ' gene by other genes which permit detection to be achieved.

Among the different hirudins which can be prepared and used, according to the invention, the following must be mentioned:

a) the hirudin corresponding to variant 2, known as HV1, the structure of which corresponds to that shown in FIG. 1 with or without the —$SO_3H$ radical;

b) the hirudin corresponding to a modification of variant 1, in which the val—val N-terminal sequence has been replaced by ile-thr;

c) the hirudin corresponding to variant 1, known as HV2, the structure of which corresponds to that shown in FIG. 18b.

The structure of corresponding genes can be deduced from that of the amino acids, as will be shown in the examples. These genes can be synthesized by any one of the known methods for preparing synthetic DNA.

The hirudin in which the N-terminal structure corresponds to ile-thr will preferably be used. Different structures of the corresponding gene will be seen in the examples.

The present invention relates to the cells, especially the bacteria and, in particular, the strains of E. coli, transformed by the vectors according to the invention and using known techniques, some of which will be recalled in the examples.

Finally, the invention relates to a process for the preparation of hirudin or its analogs, in which bacteria transformed as described above are cultured on a culture medium, and in which the hirudin or analog formed is then recovered.

The culture media employed are known to those versed in the art, and should be suited to each strain cultivated. Culturing will preferably be performed in the presence of the antibiotic against which the transformed strain has become resistant.

The hirudin or its analogs can be purified or pre-purified from the fermentation mixture by being heated at an acid pH, in particular at 50°–80° C. and at a pH between 1 and 3, especially at 70° C. and at pH 2.8, with recovery of the supernatant in which the hirudin is present.

It is also possible to turn to account the affinity of hirudin for thrombin using a resin to which thrombin is bound, and passing the mixture containing hirudin over such a resin. The hirudin is bound and this can then be eluted with a solution containing a competitive agent for hirudin.

The present invention finally relates to the hirudin or analogs thereof obtained by carrying out the process according to the invention, that is to say, the hirudin or analogs thereof of bacterial origin, but also the hirudins or analogs obtained from bacterial products by chemical or enzymatic reaction, for example, by chemical or enzymatic cleavage or, alternatively by chemical or, enzymatic reaction designed to bind an —SO$_3$H radical.

In particular, the invention relates to the peptides containing all or part of the following formula:

| ATT | ACT | TAC | ACT | GAT | TGT | ACA | GAA | TCG | GGT | CAA | AAT | TTG | TGC |
|-----|-----|-----|-----|-----|-----|-----|-----|-----|-----|-----|-----|-----|-----|
| Ile | Thr | Tyr | Thr | Asp | Cys | Thr | Glu | Ser | Gly | Gln | Asn | Leu | Cys |
| CTC | TGC | GAG | GGA | AGC | AAT | GTT | TGC | GGT | AAA | GGC | AAT | AAG | TGC |
| Leu | Cys | Glu | Gly | Ser | Asn | Val | Cys | Gly | Lys | Gly | Asn | Lys | Cys |
| ATA | TTG | GGT | TCT | AAT | GGA | AAG | GGC | AAC | CAA | TGT | GTC | ACT | GGC |
| Ile | Leu | Gly | Ser | Asn | Gly | Lys | Gly | Asn | Gln | Cys | Val | Thr | Gly |
| GAA | GGT | ACA | CCG | AAC | CCT | GAA | AGC | CAT | AAT | AAC | GGC | GAT | TTC |
| Glu | Gly | Thr | Pro | Asn | Pro | Glu | Ser | His | Asn | Asn | Gly | Asp | Phe |
| GAA | GAA | ATT | CCA | GAA | GAA | TAT | TTA | CAA |     |     |     |     |     |
| Glu | Glu | ILe | Pro | Glu | Glu | Tyr | Leu | Gln |     |     |     |     |     |

This peptide is shown with the corresponding coding sequence which does not form part of the peptide.

The invention also relates to the variants of hirudin HV1 and HV2 as shown in FIG. 18.

The invention relates, finally, to pharmaceutical compositions containing hirudin or its analogs as an active principle.

These compositions can be administered intraperitoneally, intravenously, intramuscularly, subcutaneously, orally or by topical cutaneous administration.

These compositions contain the excipients known in this field, and optionally other active principles.

The present invention naturally includes other aspects, in particular certain plasmids which will be described in the examples, as well as the mutants and derivatives thereof and, in general, the processes of fermentation of the transformed bacteria, as well as the products thereby obtained.

Other characteristics and advantages of the invention will be more fully understood on reading the examples below and the attached diagrams, wherein:

BRIEF DESCRIPTION OF THE DRAWINGS

FIG. 1 shows the amino acid sequence of hirudin extracted from a whole leech.

FIG. 2 shows the 48-mer oligonucleotide probe designed for the screening.

FIG. 3 shows the hirudin sequence of the clone pTG717.

FIG. 14 shows the preparation of pTG941.

FIG. 15 shows the preparation of pTG951

FIG. 18 shows amino acid sequences of HV1 and HV2.

Figure 4:
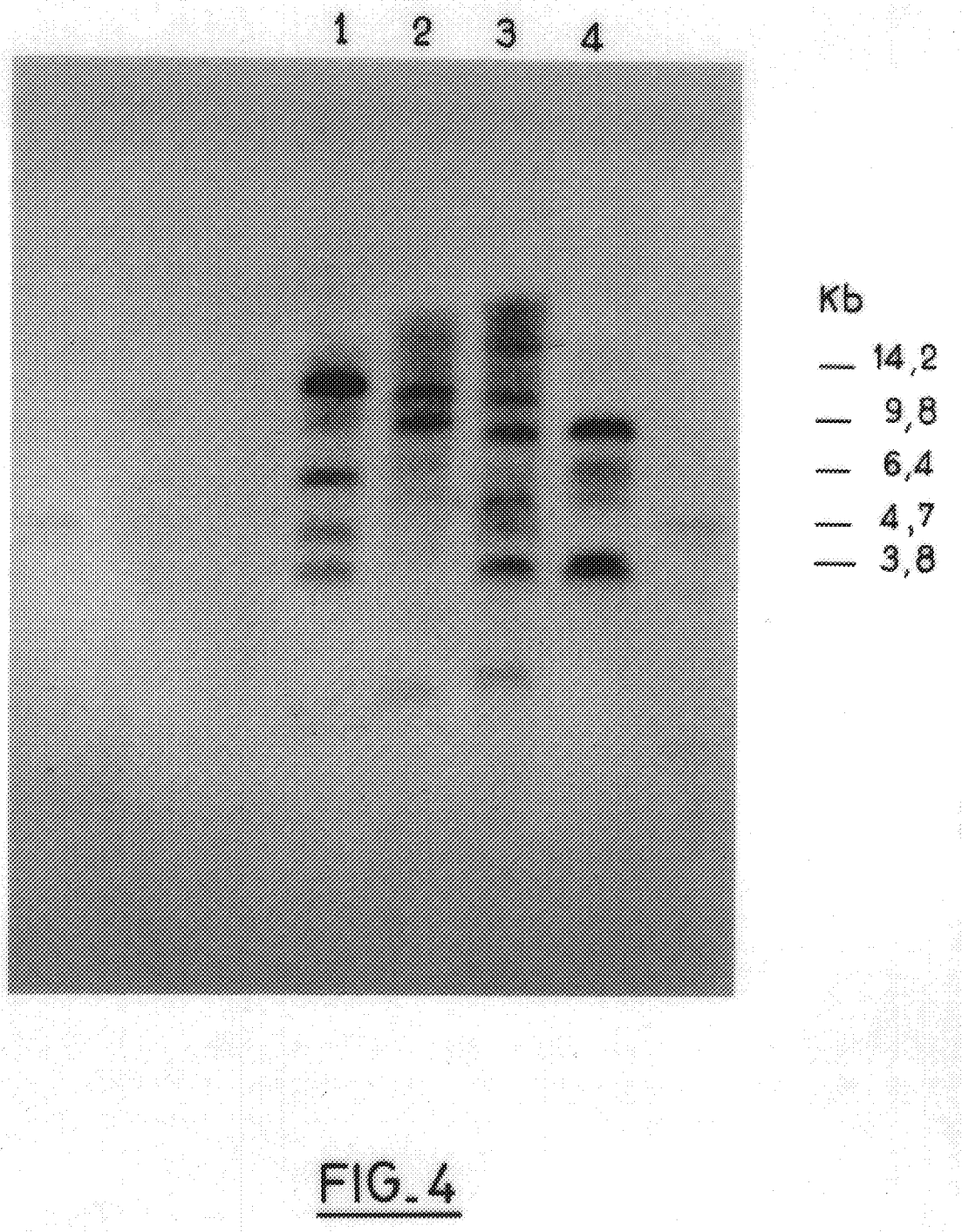
FIG. 4 shows an autoradiograph of the hybridization mixture between the labeled probe and various pTG717 restrictions.

It is appropriate to note that the different nucleotide sequences appearing in the diagrams must be considered to form an explicit part of the present description, these sequences not having been reproduced in the body of the text so as not to encumber it needlessly.

Most of the techniques employed in the following examples are known to those versed in the art, and some are described in the attached references, only the special techniques will be discussed in the course of the description. The characteristics of the strains used will only be given by way of general information

Bacterial strains

The bacterial strains used in the context of the present invention are as follows:

TGE900, an *E. coli* strain having the following characteristics: su F his ilv bio (λcI857ΔBamΔHI).

N6437, an *E. coli* strain having the following characteristics: F$^-$ his ilv gal$^+$ Δ8proC$^+$: tn10 lac Δ m15 (λcI857ΔBamΔHI).

Jm103, an *E. coli* strain having the following characteristics: Δ (lac-pro) sup$^E$ thi endA sbcB15 sttA rK$^-$ nK$^+$/F$^1$ traD36 proAB$^+$ laci$^a$ lacZΔm15.

The strains mentioned above were used because they were available, but it is obvious that it is possible to use other strains, provided that the strains have certain essential characteristics which are recalled in the course of the detailed description.

The examples below essentially comprise the following stages:
1) the preparation of mRNA molecules and the formation of a cDNA library;
2) the production of a probe;
3) the selection of the library by means of this probe and the identification of a plasmid carrying the sequence coding for hirudin;
4) the production of a vector for the expression of the gene coding for hirudin;
5) a study of the results obtained.

Preparation of the RNA

Living leeches of the species *Hirudo medicinalis* are collected in the Bordeaux region of France. They fasting for a minimum of 4 weeks and then are decapitated, with the heads being immediately frozen in liquid nitrogen. The whole head RNA is extracted by grinding the heads into the form of a fine powder in liquid nitrogen. To 1 g of this powder, 5 ml of an NETS buffer (10 mM Tris HCl, pH 7.5, 100 mM NaCl, 1 mM EDTA, 0.5% SDS) and 5 ml of redistilled phenol are added, both being preheated to 95° C. The solution is then mixed by means of a vortex and centrifuged at 30,000 g, the aqueous phase is re-extracted with 1 ml of NETS buffer and the combined aqueous phases are re-extracted with 5 ml of fresh phenol. The RNA is precipitated by adding two volumes of ethanol and collected by centrifugation after the mixture has been left at –20° C. for over 4 hours. The dark brown pellet is dissolved in 2.5 ml of distilled water, 2.5 ml of 5M LiCl are added, and after being mixed, the solution is left overnight at 4° C. The solution is then enriched with 5 ml of 3M LiCl and centrifuged at 20,000 g for 10 minutes at 4° C. The supernatant is removed and the pale RNA pellet taken up in 1 ml of water. It is taken up in 0.25M NaCl and the RNA is precipitated with 2 volumes of ethanol. The final RNA pellet is recovered by centrifugation and then dissolved and stored at –80° C. in distilled water. The RNA concentration is measured by its absorption at 260 nm.

Polyadenylated messenger RNA is prepared using an oligo(dT)-cellulose and a standard procedure (22). The yield of mRNA represents approximately 2 to 5% of the total starting RNA.

Preparation of complementary DNA and construction of the cDNA library in the vector plasmid pBR 322

The process employed is exactly the same as that which led to the construction of the human liver mRNA library described in reference 23. The leech head mRNA molecules are copied into DNA form using an oligo(dT) "primer" and the enzyme reverse transcriptase. A second strand of DNA is synthesized using DNA polymerase, the hairpin is opened with S1 nuclease and the double-stranded cDNA is purified on a sucrose gradient. cDNA molecules of specified size are terminated at the 3' end with small dC extensions using the enzyme terminal deoxytransferase, and are then united with a pBR322 vector having a polyG end cut by Pst1. The plasmids obtained are used to transform *E. coli* strains (strain 1106), and the tetracycline-resistant transformants (obtained with an efficiency between 500 and 1,000 per ng of double-stranded cDNA) are grown on L-agar plates containing 15 μg/ml of tetracycline. A cDNA clone library representing 43,000 individual transformants is established, and the cells are recovered from the colonies by scraping and resuspended in an L-broth containing tetracycline. A suspension is made in 50% strength glycerol and stored at –20° C.

Production of the DNA probe for screening the library

In view of the fact that the amino acid sequence published for hirudin (FIG. 1) does not have methionine or tryptophan, that is to say, the amino acids which are encoded by a single codon, the protein sequence does not have regions which are particularly propitious for producing especially short oligonucleotide probes which, as a general rule, constitute the strategy employed for identifying cloned DNA sequences (24). For this reason, it was decided to adopt the different technique of using a single but rather large oligonucleotide probe, and this made it possible, in particular, to isolate the cDNA clone for human clotting factor IX (23). Using this strategy, the amino acid sequence region is selected for in which the redundancy of the codons is limited to the choice of the 3rd base (that is to say, arginine, leucine and serine are avoided), and the 3rd base is selected. The parameters in question for choosing the 3rd base of this codon are known, and it is a question of maximizing the possibility of G/T interaction and avoiding hairpins and palindromes in the probe sequence, and of course, of taking into account the known gene sequences for leeches.

Since no gene sequence has been published for leeches, it was necessary to make use of the knowledge available in respect to the organisms closest to the leeches from the evolutionary standpoint, and for which many published DNA sequences exist, i.e., insects. Accordingly the coding sequences for insect DNA molecules were analyzed and a table was drawn up of the codons which arise most frequently. Together with other parameters, this was used to design an oligonucleotide 48 bases long, corresponding to 16 amino acids, from position 34 to position 49 in the hirudin sequence. This sequence region shows redundancy only in the third position of each codon.

This oligonucleotide, shown in FIG. 2, was synthesized chemically by the phosphodiester method, on an inorganic solid support (25), which has already been described for a reference 52-mer (23).

Screening of the cDNA library with the 48-mer oligonucleotide

The cDNA library formed from the leech head mRNA molecules is plated on L-agar plates containing 15 μg/ml of tetracycline with a colony density of approximately 4,000 colonies per 13-cm plate, and the colonies are grown to a size of 1 to 2 mm in diameter at 37° C. The colonies are then withdrawn onto nitrocellulose filters. The colonies on the maintained plates are grown and the plates are then stored at 4° C. The filters are placed on plates of L-agar containing 170 μg/ml of chloramohenicol and incubated overnight at 37° C. to amplify the plasmids in the bacterial colonies. The filters are then treated using the standard procedure to lyse the bacterial colonies and bind the DNA to the nitrocellulose. The filters are then washed very thoroughly and then prehybridized in a volume of 100 ml of 6×SSC (1×SSC=

0.15% NaCl, 0.015M trisodium citrate), 5×Denhardts (1×Denhardts solution=0.02% Ficoll, 0.02% of polyvinylpyrrolidone, 0.02% of bovine serum albumin) 100 μg/ml of yeast transfer RNA and 0.05% of sodium pyrophosphate.

An aliquot (30 pmol) of the 48-mer oligonucleotide is labeled with [$^{32}$P] at its 5' end by incubation with Γ[$^{32}$P]ATP in the presence of 15 units of polynucleotide kinase. The labeled probe is purified from free Γ[$^{32}$P]ATP by passage on DEAE-cellulose.

The labeled probe is hybridized on the filter at a dose of 20 ml of 6×SSC, 1×Denhardts, 100 μg/ml of yeast tRNA, 0.05% of sodium pyrophosphate at 42° C. with gentle agitation for 16 hours.

The filters are then washed in 6×SSC, 0.1% of sodium dodecylsulfate (SDS) at a temperature of 37° C., 42° C. and 50° C., and then subjected to a final wash with 2×SSC, 0.1% SDS at 50° C. for 10 minutes. The filters are then dried and exposed on X-ray films. The colonies giving positive results are identified from the labeled plates by comparing the positive spots on the X-film with the master plates. One of these clones, the plasmid of which will be referred to as pTG700, is confirmed as positive by a second hybridization with the labeled probe and is cultured in quantity, and the plasmid DNA is purified using standard procedures.

Identification of pTG700 as containing the sequence coding for hirudin

The cDNA insert of pTG700 represents approximately 235 base pairs. This DNA fragment is isolated and transferred into the vector phage m13 mp8, and the DNA sequence of the insert is determined by chain termination (26). A portion of this sequence codes for a protein sequence which is very similar to that of hirudin. This region of the sequence corresponds to the zone of the probe which is shown in FIG. 2.

In FIG. 2:

(a) corresponds to the hirudin sequence which appears in reference 2 from glu 49 to gly 34, (b) corresponds to the sequence of the 48-mer probe synthesized and used for the hybridization, (c) corresponds to the sequence of the clone pTG700 in this region, the dots indicating the homologies, and (d) corresponds to the amino acid sequence coded in this region of pTG700.

It should be noted that the cDNA sequence in pTG700 is incomplete, as it encodes only 28 of the C-terminal amino acids of hirudin, in addition to the 101 base of the 3' non-translated sequence preceded by a stop codon in phase. One of the differences relative to the published protein sequence for hirudin is observed in this clone, since glutamic acid replaces glutamine at position 49.

Isolation of clones of larger hirudin cDNA

Since the DNA sequence confirms that the pTG700 insert codes for hirudin, this insert is made radioactive with [$^{32}$P] using the known "nick translation" procedure and is used for a new test on the cDNA library. Several other positive colonies are found and one of these contains a plasmid designated pTG717, which contains an insert of approximately 450 base pairs in length. Restriction analysis of this insert shows the presence of a Taq1 restriction site situated in the region of the center.

For this reason, the purified fragment is digested with Taq1 and the resulting 5' and 3' fragments are linked in the sequencing vector m13 cleaved with PstI/AccI. The construction of m13 contains each of the fragments which can be identified and subjected to sequential analysis. The result of this analysis is shown in FIG. 3. The DNA sequence of the pTG717 insert, minus the polyG/C ends introduced at the chain end during the cloning step of the procedure, is 379 bases long. Of the bases, 219 code for a peptide whose sequence is very similar to that of the published hirudin sequence.

Various points must be noted in this sequence.

1) The amino acid sequence encoded by the fragment is not identical to that of the published protein sequence for native hirudin. There is a difference of 9 amino acids between the hirudin sequence isolated from pTG717 and the published hirudin sequence. The following modifications are noted: Val 1-ile; val 2-thr; gin 24-lys; asp 33-asn; glu 35-lys; lys 36-gly; lys 47-asn; gln 49-glu and asp 53-asn. These modification constitute a major change in the sequence, since 7 of the modifications involve a change in charge. The homology between the cloned coding sequence and the published protein sequence is thus 46/65, that is to say, approximately 70%.

There are two possible reasons for the observed differences between the two amino acid sequences.

1 Species, subspecies and even individual animal variations can be seen between the exact sequence of the hirudin molecule. It is not possible to verify whether the leeches used in this study are exactly of the same species or subspecies as those which were used to publish the amino acid sequence. Furthermore, it is possible that there exists in leeches not only one but various forms of hirudin, with similar biological activity but with variations in the fundamental amino acid sequence. In this context, there should be noted to the differences in the results in the literature relating to the N-terminal amino acids of hirudin (originally, ile had been found in the material from the heads, and then val had been found in the animal as a whole, while more recently, ile was indicated again as originating from the heads). Isoleucine is present in the pTG717 sequence at the position corresponding to the N-terminal end of the mature protein.

The concept of different forms of hirudin is supported by the preliminary studies at the DNA level. When leech total DNA is extracted from ground frozen leeches using standard procedures, digested with various restriction enzymes, treated by electrophoresis on agarose gel and then transferred to nitrocellulose and hybridized with the pTG717 insert as a probe, a large quantity of fragments which hybridize is observed.

Thus, the results in FIG. 4 are obtained in the following manner:

10 μg of the leech total DNA are digested with restriction enzymes and pressed to electrophoresis on a 1% agarose gel, transferred to nitrocellulose filters and hybridized with a [$^{32}$P]-labeled pTG717 PstI insert. The filters are then washed thoroughly (0.1×SSC, 0.1% SDS, 65° C. and the hybridized bands are visualized using autoradiography.

Lane 1—DNA digested with EcoRI

Lane 2—DNA digested with HindIII

Lane 3—DNA digested with BamHI

Lane 4—DNA digested with BglII

The size of the EcoRI fragments in kb is indicated at the right.

With the Eco R1 digestion fragments, 6 fragments totaling 40 kb can be seen under very stringent washing conditions.

Even if it is theoretically possible that this scheme represents a very broad mosaic gene, it is unlikely that a single small sequence coding for fewer than 400 bases is distributed over 40 kb of genome. Furthermore, preliminary experiments with probes containing partial insert fragments suggest that this is not the case.

It was also observed that there was a difference in the sequences in different clones of hirudin isolated from the same cDNA library. For example, in pTG700, a lys is found in position 47 (FIG. 2), as in the published amino acid sequence, while in pTG717, there is an asn at this position.

For this reason, all these data are consistent with the concept of hirudin genes of different structure, showing multiple forms at the protein level.

A further point which is important is that the whole hirudin mRNA sequence is certainly not present in pTG717. In effect, open reading continues up to the 5' end of the clone, and there is no methionine in this region. Since hirudin is a protein which is secreted from cells of the salivary glands, it is likely that it has, at its N-terminal end, a leader sequence (needed for secretion) and probably also a pro-sequence. The final active molecule would then be produced, as is the case for many zymogens and precursors, by proteolytic cleavage stages.

The size of the hirudin mRNA was determined, and confirms that the clone pTG717 is not a complete copy thereof. Hirudin total head RNA was subjected to electrophoresis on agarose gel denatured with formaldehyde (27), transferred to nitrocellulose and hybridized with a PTG717 insert. A single, 640 base pair hybrid RNA species is observed. Since it is thought that pTG717 contains the whole 3' mRNA sequence (a polyA portion is observed), and likewise, two polyA addition sites which overlap, approximately 20 base from the polyA, a 160 bp 3' non-translated region is seen (FIG. 3). This cDNA clone lacks 160 base pairs at the 5' end. It contains the remainder of the N-terminal end of the protein, the methionine of the initiator and a 5' non-translated region of the mRNA. It cannot be ruled out that hirudin is cut from the C-end in the form of a larger precursor, which can code for other biologically active peptides, although the maximum size of this hypothetical precursor would be at least 110 to 120 amino acids (that is to say, approximately twice the size of mature hirudin).

It was not possible to generate cDNA clones longer than pTG717, and it is thought that a secondary structure in the 5' end of the mRNA prevents reverse transcription of the mRNA beyond this point. Analysis of the genomic sequence of hirudin should provide data on the 5' end of this gene.

The amino acid sequence of hirudin encoded by the clone pTG717 was adapted so as to be expressed in *E. coli* cells, in the manner to be described below.

Expression of hirudin in *E. Coli*

Figure 5:
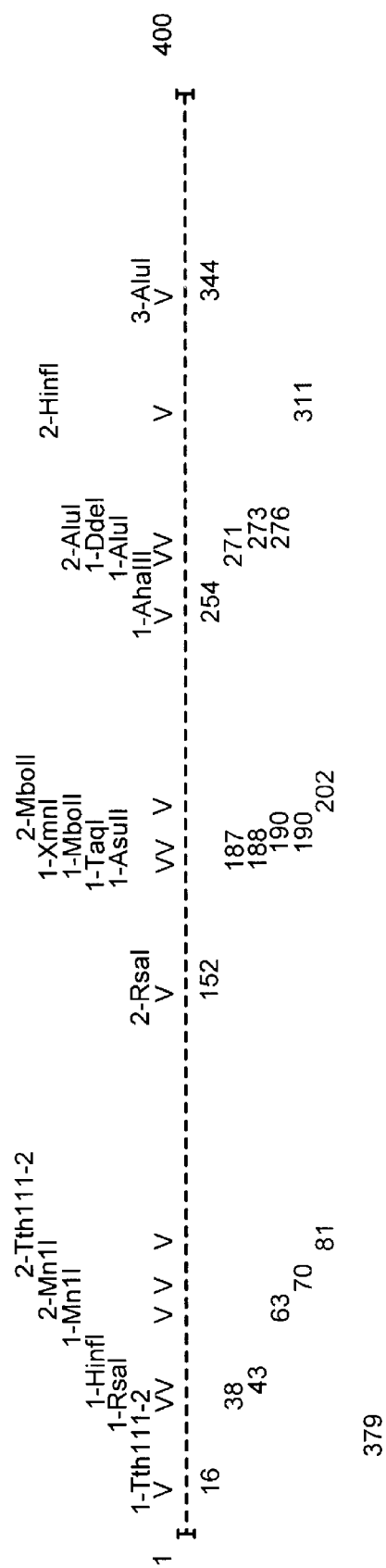
FIG. 5 shows the restriction map of the insert in pTG717.

From the restriction analysis of pTG717 (FIG. 5), it is clear that the whole of the amino acid coding sequence is present in the form of a 225 bp HinfI-AhaIII fragment. This fragment is isolated by restriction and inserted in the plasmid expression vectors pTG951 and pTG927, using synthetic oligonucleotide adaptor molecules. The adaptors constitute the 7 amino acids which are removed from the N-terminal end by HinfI restriction, and the initiator methionine fragment and the site for the restriction endonucleases NdeI or BglII, which are required for insertion in the expression vectors, are added.

The two amino acids after the met initiator are replaced, that is to say, the ile-thr fragment which appears in the pTG717 cDNA clone is replaced by val—val of the published hirudin protein sequence.

Although the pTG717 cDNA clone contains the ile-thr sequence instead of the val—val sequence of the published sequence for hirudin, it was initially decided to express the molecule with a val—val sequence at the N-terminal end. There are two reasons for this choice:

the cDNA clone is certainly incomplete, there probably being a secondary structure in the mRNA which prevents transcription; this makes it possible for the 5' end of the cDNA sequence to be incorrect, taking into account the transcription and cloning of "arti-facts"; and it is generally accepted that the N-terminal end of the active hirudin molecule extracted from the whole animal begins with val—val (8, 11).

The expression vector pTG951 is a plasmid expression vector designed to express the interferon-Γ gene, the synthesis of which is recalled at the end of the present description.

Figure 6:
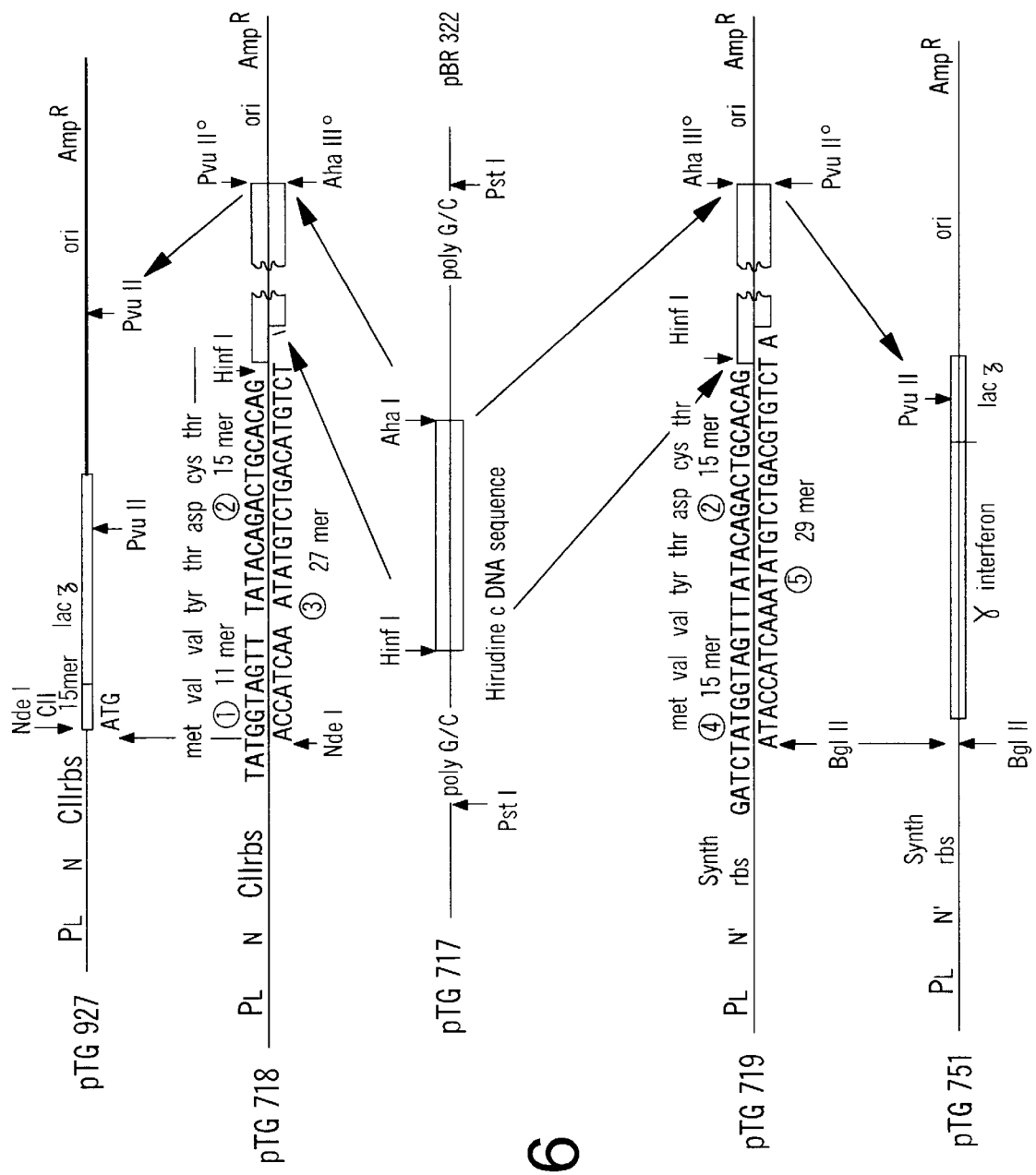
FIG. 6 shows, in detail, the construction of the two vectors for the expression of hirudin, pTG718 derived from pTG927 and pTG719 derived from pTG951.

In practice, it contains, in essence, the bacteriophage leftward promoter $P_L$ controlled by a repressor encoded by the temperature sensitive host C1857, followed by the N gene of λ, intact or truncated. A site for binding synthetic ribosomes is then present, this being designed to give optimal binding of ribosomes. A single BglII restriction site is present located between the ribosome binding site and the ATG of the sequence coding for interferon-Γ. This vector is digested at the BglII site and at the single PvuI site downstream of the sequence coding for interferon-Γ, and is then recovered by electrophoresis on agarose gel. This vector fragment is combined with an adaptor oligonucleotide assembly and the hirudin sequence containing the HinfI-AhaIII fragment, as described in FIG. 6.

The expression vector pTG927 is closely related to the expression vector pTG908 described at the end of the present description. It differs only in that it contains an additional SalI-PvuII fragment originating from the tetracycline gene of pBR322. The expression vector pTG927 contains the promoter $P_L$, an intact N gene and the ribosome binding site of the Γ CII protein, then the ATG and a sequence coding for the lacZ fragment of β-galactosidase. An NdeI site is found on the ATG of this coding sequence. This vector is digested with NdeI and PvuII and the vector fragment is purified. It is used together with another oligonucleotide adaptor combination and the HinfI-AhaIII fragment of hirudin to construct the second hirudin expression vector shown in FIG. 6. The two expression vectors are designed to express the native hirudin molecule (with a val—val sequence at the N-terminal end immediately after the ATG initiator).

In the adaptor oligonucleotide, the codon of the 3rd base is chosen to promote a high degree of translation and to avoid the formation of secondary structures in the mRNA at the level of this region.

The two vectors are assembled in the following manner: the oligonucleotides are phosphorylated at the 5' end with polynucleotide kinase, and then treated in an equimolar mixture (after 10 minutes' heating at 65° C., for 15 hours at 15° C.). The vector and the hinrudin fragment are provided in amounts designed to give mol ratios of vector/hirudin fragments/adaptor fragments of 1:20:50, and the mixture is ligated with T4 DNA ligase. The ligation mixture is used to transform *E. coli* strain TG900 and the transformants carrying the plasmids are selected on an agar plate containing ampicillin (100 ug/ml), and those which contain the sequence coding for hirudin are identified by hybridization of the colonies using a labeled pTG717 insert as probe. From a large number of positive clones, 6 of each, as well as 1 negative (parent strain), are selected and grown in an L-broth liquid medium at 30° C. to an optical density of 0.3 at 650 nm. Expression starting from the $P_L$ promoter is then induced by increasing the temperature to 37° C. and an incubation which is maintained for 6 hours. The cells are then harvested by centrifugation suspended in ⅕ of the volume of TGE (25 mM Tris HCl, pH 8, 50 mM glucose, 10 mM EDTA) and then ground by sonication. After clarification of the extracts by centrifugation, an aliquot of the supernatant is tested for its antithrombin activity. Significant levels of antithrombin activity appear in 5 of the 6 constructions with pTG927 and in 4 of the 6 constructions with pTG951, which also show activity although this is weaker.

The controls do not show any significant activity. Analysis of the DNA sequence of the clones giving positive results by direct sequencing of the plasmids shows that the expected sequence is present in all the constructions which show activity.

Figure 7:
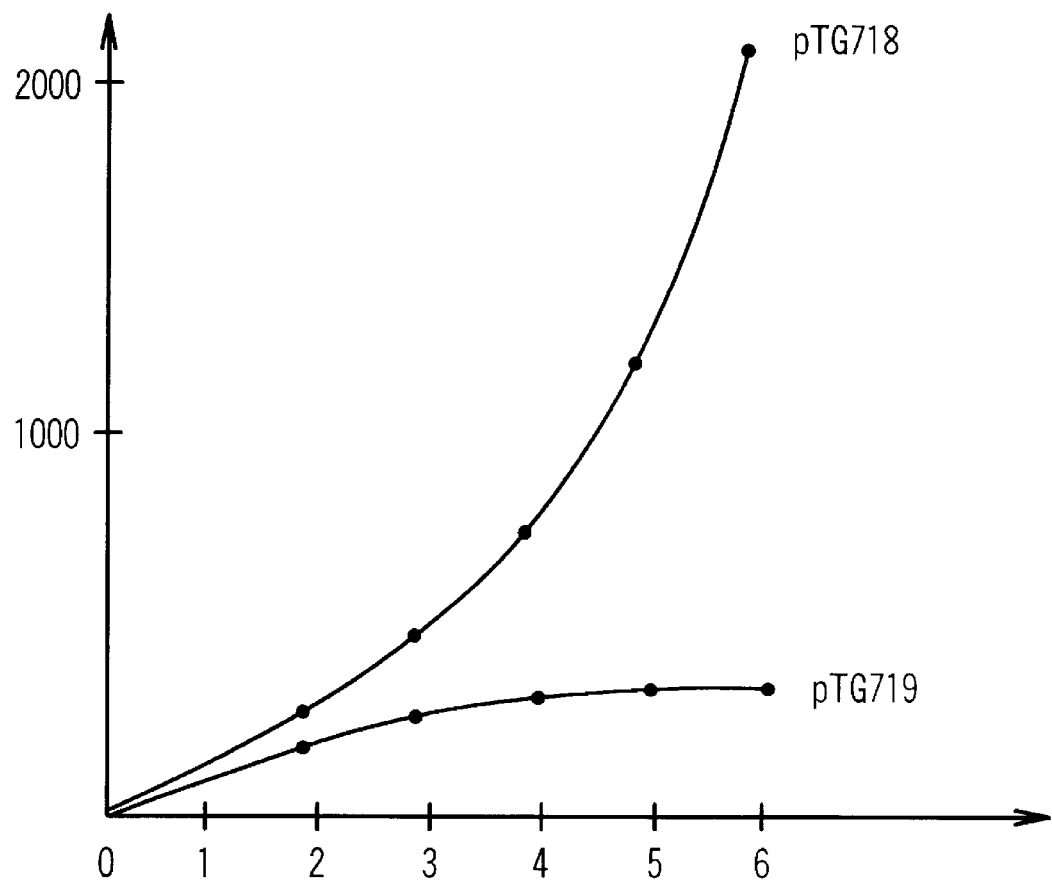
FIG. 7 shows in a graph, the changes in the hirudin activity with respect to time in the *E. coli* extracts for the two vectors.

Two clones showing positive expression, the clone pTG719, derived from pTG951, and the clone pTG718, derived from pTG917, are analyzed for 6 hours of induction. After growth of the culture at 30° to an optical density of 0.3, expression is induced by raising the temperature to 37° C., and an aliquot is withdrawn every hour for 6 hours from the extracts as prepared above, and the hirudin activity is measured (29). It is seen from the results (FIG. 7) that the clone pTG719 shows an initial growth followed by a plateau of activity after 3 to 4 hours, which is at the level of 370 U/l at an optical density of 650.

In contrast, the clone pTG718 shows greater activity, which continues to increase throughout this entire induction period.

The level of activity obtained after 6 hours is approximately 5 times greater than that of the clone pTG719, and represents a total activity of 7300 μ/l of culture. If this hirudin recombinant shows specific activity similar to that of the natural val—val product, the product obtained in the most active extracts would correspond to approximately 1 mg/l of culture.

Property of the hirudin obtained

In order to characterize the hirudin obtained from *E. coli*, analysis was performed directly on culture samples after induction, which were heated to 70° C. for 15 min or heated to 70° C. after reduction of the pH to 2.8 with HCl. In the latter case, the pH of the extract was brought back to neutral before being assayed. Native hirudin treated in the same manner shows no loss in activity, as could be expected in light of published material on the properties of the molecule (20). In the case of the extract, no loss in activity is seen after this treatment, in fact, after the treatment, an approximately 2-fold increase in activity is observed. This can reflect either the degradation or the inactivation of constituents of the extract which inhibited the action of hirudin, or possibly the rather low pH and the heating stage may, in some cases, provide for a more complete re-forming of the disulfide bridges which are needed for hirudin to show maximum activity. The control extracts show no activity, either before or after the treatment.

When the bacterial extracts are preincubated with thrombin bound to a Sepharose resin, and the thrombin-Sepharose is removed by centrifugation, virtually all the initial hirudin activity is removed from the extract. The hirudin obtained according to the present invention appears to bind very effectively to the thrombin-Sepharose resin, and this makes it possible to envisage a possible means of purifying this bacterial hirudin.

Bacterial cultures of cells containing the expression vector pTG718 are cultured to an optical density of 0.3 at 30° C. and then induced at 37° C., and aliquots are withdrawn every hour and labeled, on minimal medium, with 100 μCi/ml of [$^{35}$S]methionine. The bacteria are collected by centrifugation and the combination of labeled bacterial proteins is analyze by electrophoresis on SDS-polyacrylamide gel, followed by fluorography.

Figure 8:
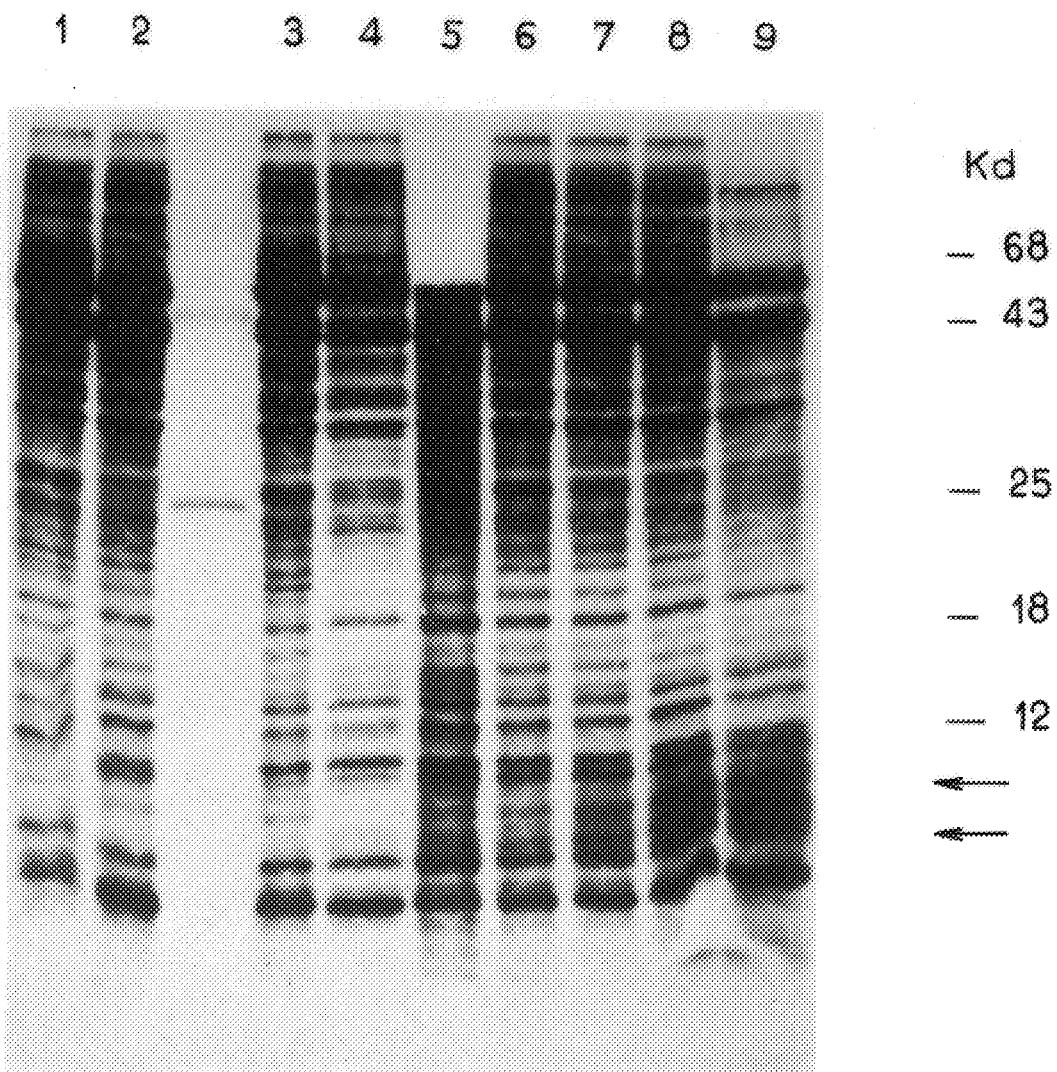
FIG. 8 shows the analysis of the labeled *E. coli* extracts containing the hirudin activity.

At least two polypeptide induced in significant quantity by the vector construction can be observed at approximately 6 to 8,000 daltons (FIG. 8—lanes 5 to 10).

Figure 9:
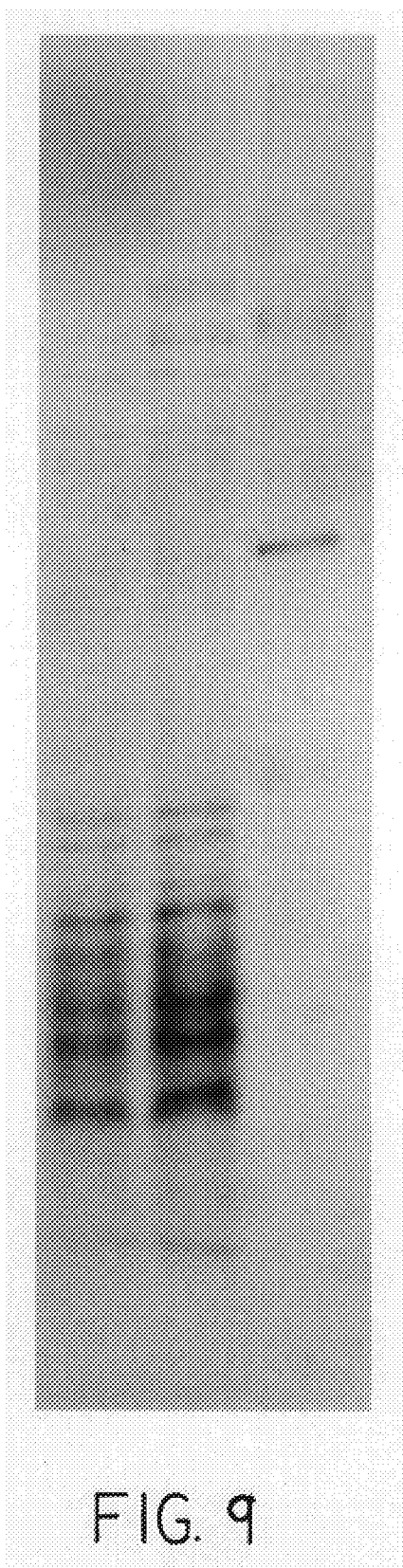
FIG. 9 shows the analysis of the same extracts as in FIG. 8, but following heat treatment at an acid pH.

When the labeled materials from non-induced pTG718 cultures and from cultures at 3 and 5 hours after induction are treated at 70° C. and at pH 2.8 for 15 min, centrifuged to remove the denatured proteins and analyzed on an SDS-polyacrylamide gel, it is clear that the bulk of the labeled *E. coli* proteins are removed from the sample (FIG. 9—lanes 1 and 2). This procedure gives a very satisfactory purification of the two bands of low molecular weight which are induced in the hirudin expression vectors.

All the hirudin activity is found in the supernatant.

Preparation of the vector plasmids pTG951 and pTG927

Figure 10:
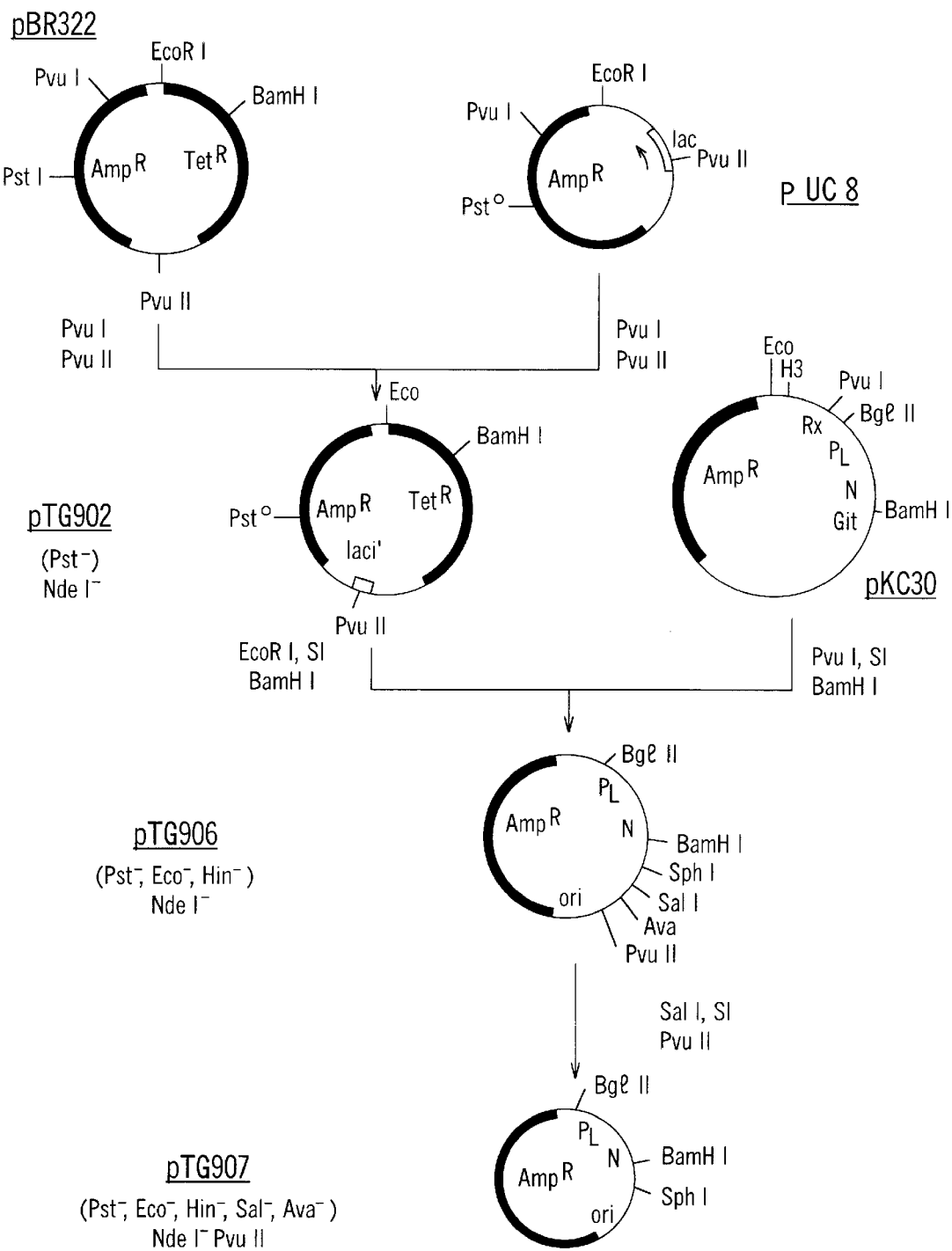
FIG. 10 shows the preparation of pTG907.

These vector plasmids have been used for cloning interferon-Γ or have been derived from plasmids which participate in the preparation of such vectors. This synthesis will be recalled briefly below in relation to the attached figures, wherein:

FIG. 10 shows the preparation of pTG907

Figure 11:
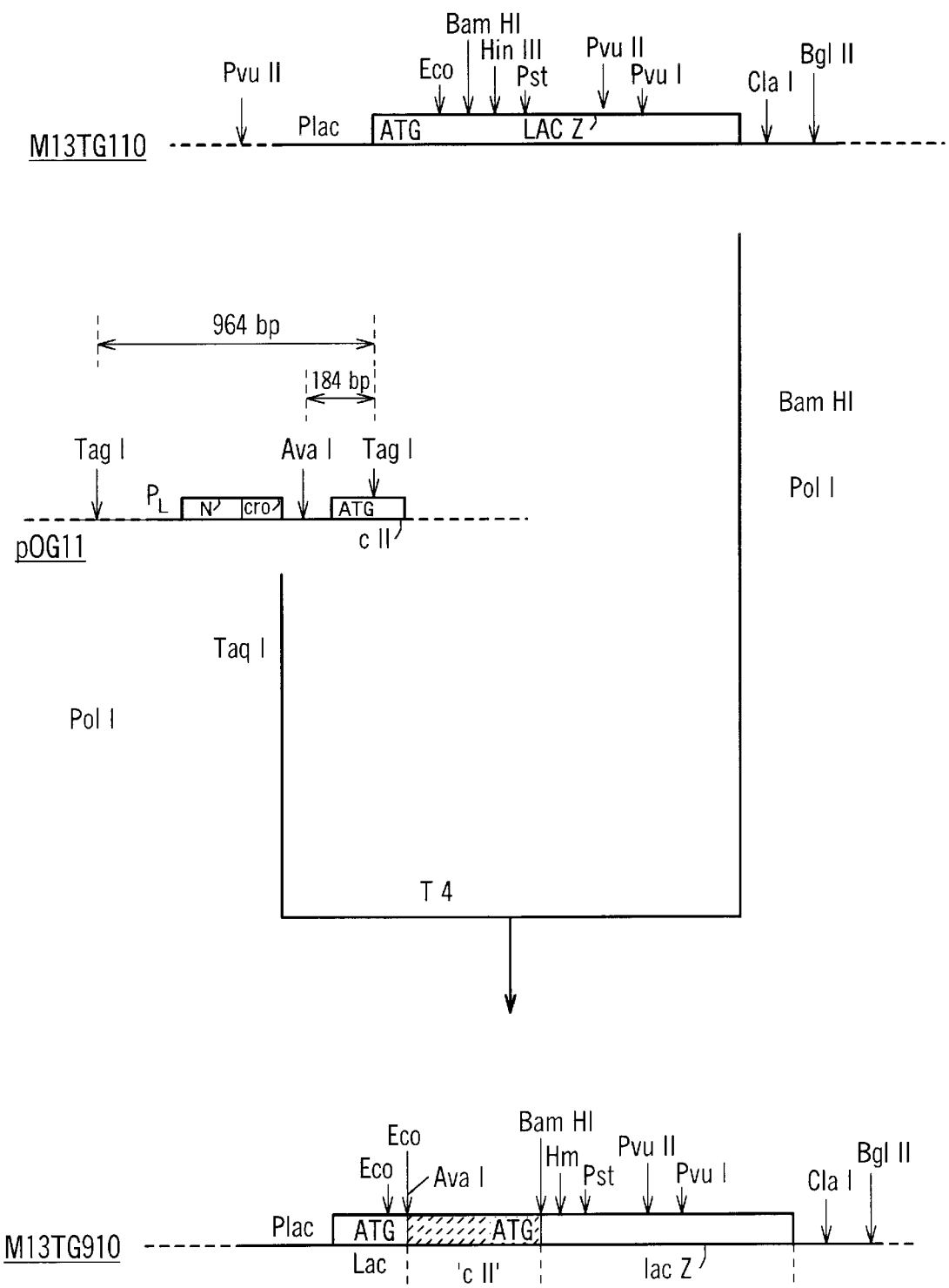
FIG. 11 shows the preparation of M13 TG 910.

FIG. 11 shows the preparation of M13 TG 910

Figure 12:
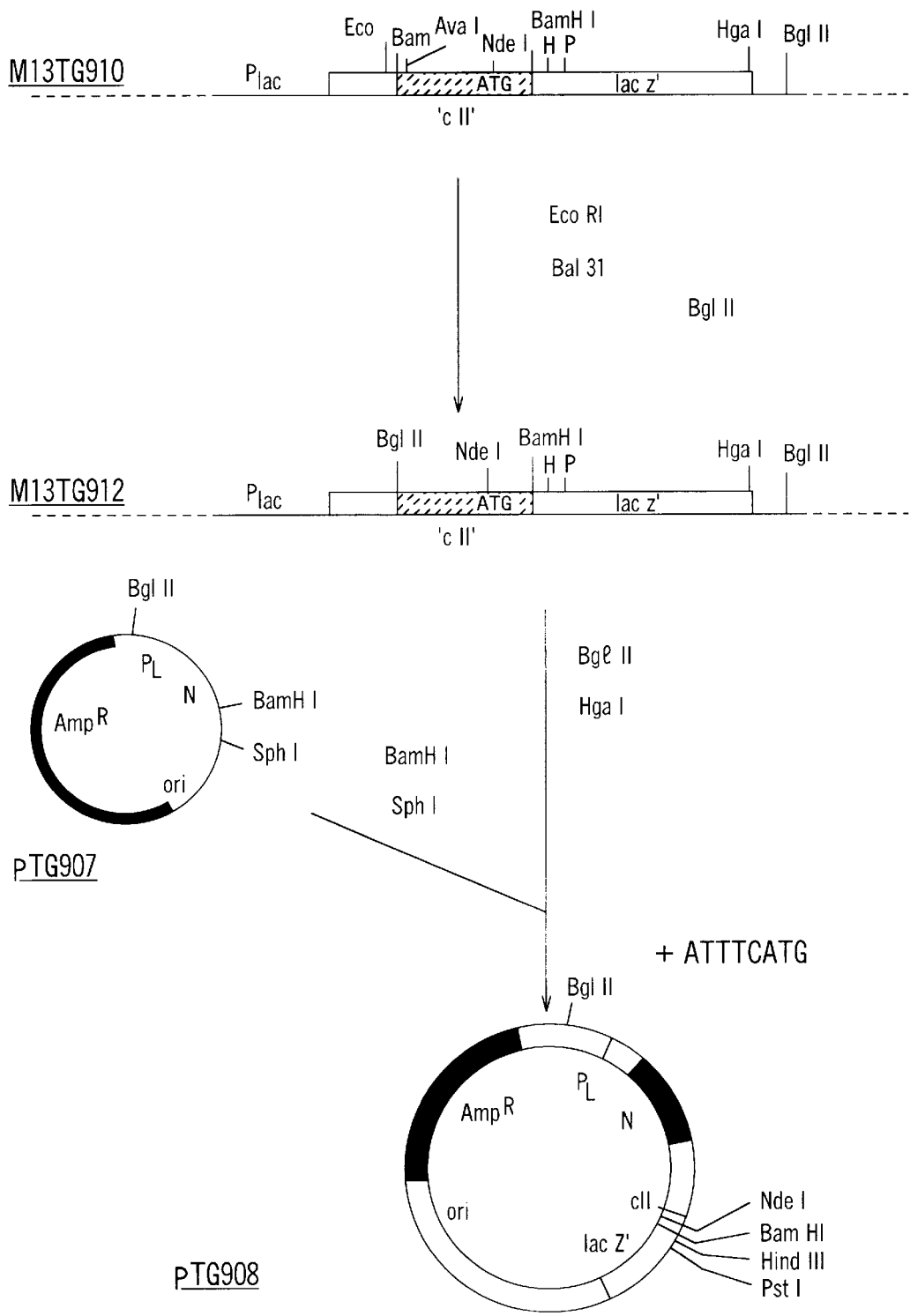
FIG. 12 shows the preparation of pTG908.

FIG. 12 shows the preparation of pTG908

Figure 13:
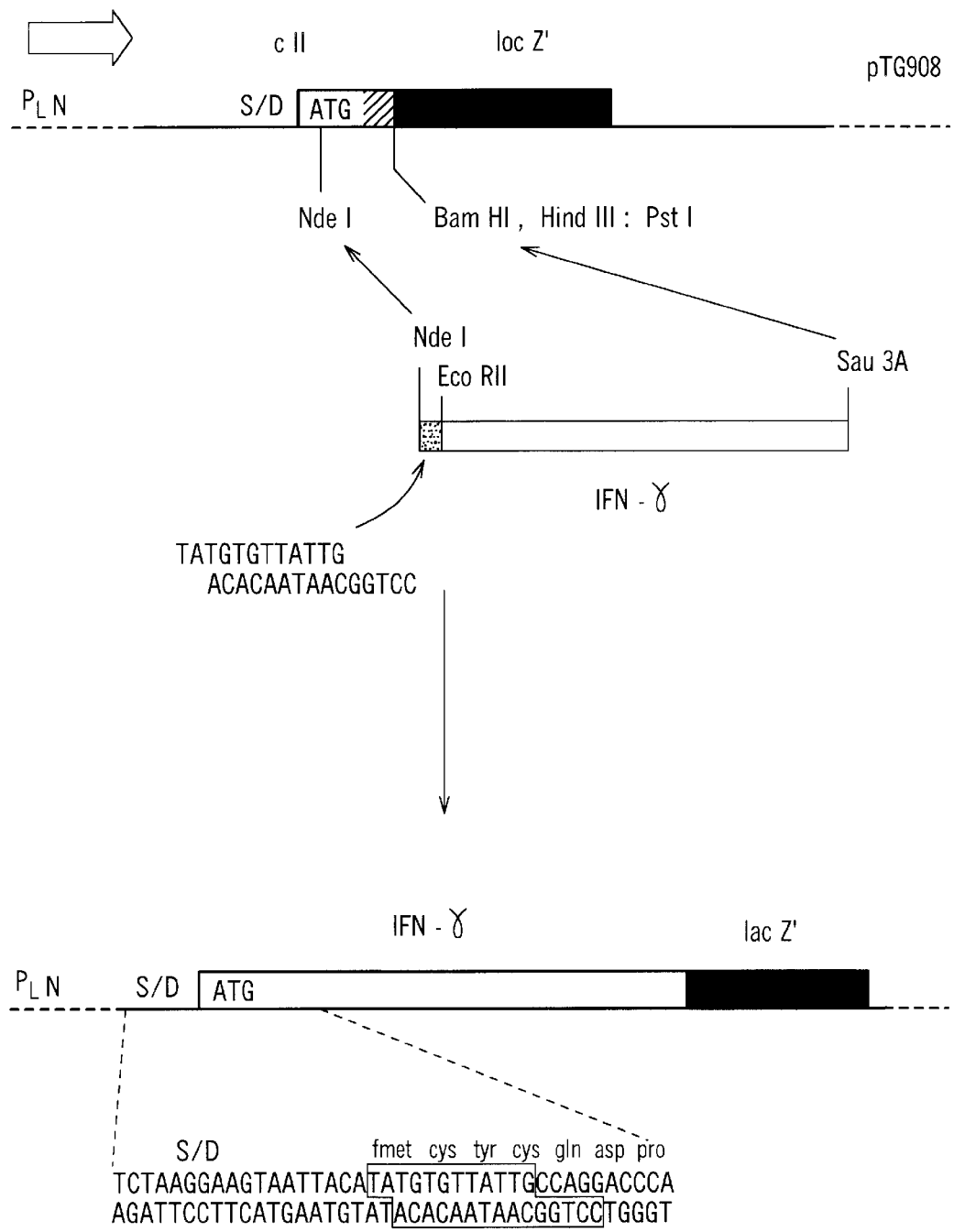
FIG. 13 shows the preparation of pTG909.
Figure 16:
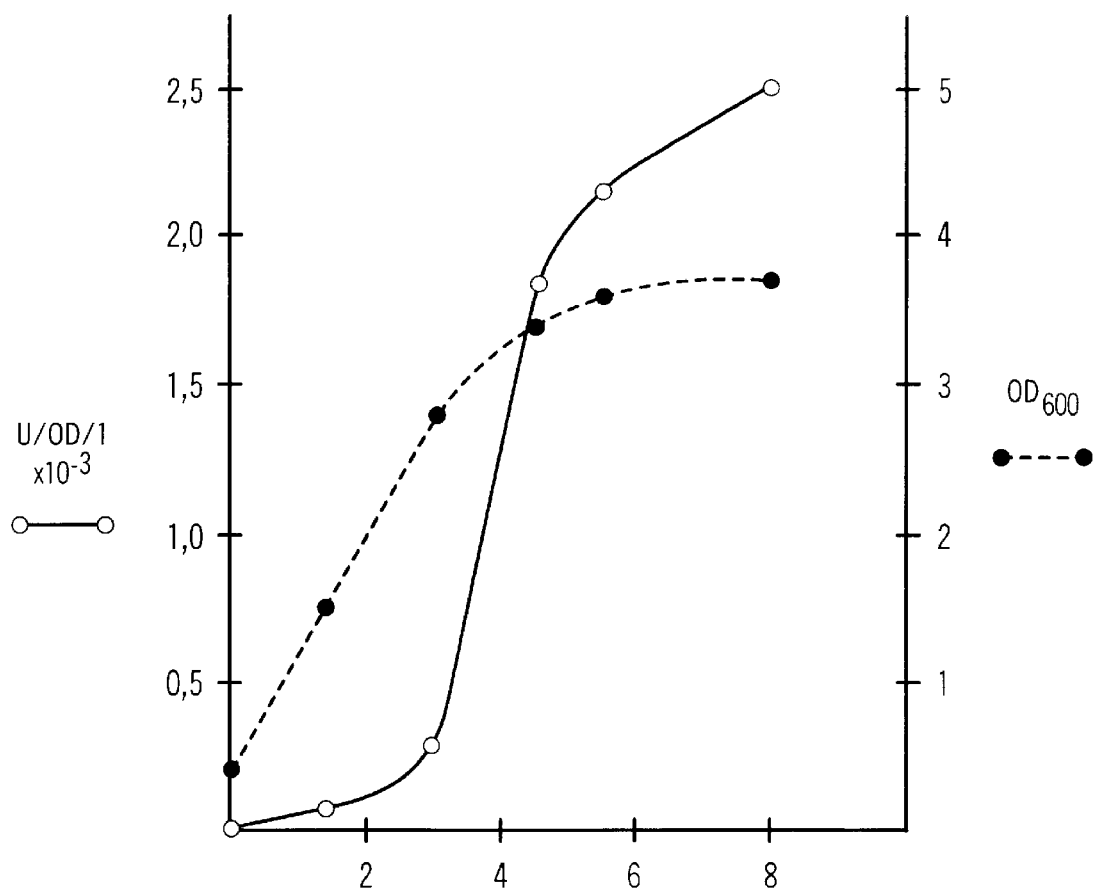
FIG. 16 shows a graph of hirudin activity induced in an *E. coli* TG900 culture containing pTG720.

FIG. 13 shows the preparation of pTG909

FIG. 14 shows the preparation of pTG941

FIG. 15 shows the preparation of pTG951.

The preparation of these vector plasmids comprises essentially:

a) the preparation of pTG908, which vector contains $P_L$, N and CII rbs; and b) the preparation of pTG951, which vector contains a binding site for synthetic ribosomes.

Preparation of pTG907 (FIG. 10)

The parent plasmid used is plasmid pBR322. However, the latter has the disadvantage of having a PstI restriction site within the amp$^R$ gene, since a site of the same nature will be used subsequently in the cloning zone as a single restriction site. Therefore, it is hence appropriate to make cause this PstI restriction site to disappear, using a mutant of plasmid pBR322, plasmid pUC8, in which the gene for resistance to ampicillin does not have a PstI restriction site (this site has been removed by mutation in vitro). pBR322 is marketed in particular by Bethesda Research Laboratories and pUC8 is described in the paper designated as reference 30.

For this purpose, the 1,669 bp PvuI–PvuII fragment of pBR322 is exchanged with the analogous PvuI–PvuII fragment of plasmid pUC8. To carry out this exchange, plasmids pBR322 and pUC8 are treated successively with PvuI and PvuII, and are then circularized by the action of a ligase.

Plasmid pTG902, which no longer has a PstI restriction site and which has also lost the NdeI restriction site present originally in pBR322 (not shown in the Figure), is thereby obtained. Furthermore, plasmid pTG902 carries a 50 kb fragment corresponding to the laci' sequence in which the PvuII site is present.

The P$_L$ promoter and the λ N gene (which originates from phage λ, the gene λ N coding for a transcription antitermination function) are isolated from plasmid pKC30 and inserted in pTG902, as shown in the attached FIG. 10, by treatment with EcoRI, S1, BamHI for pTG902 and by treatment with PvuI, S1, BamHI for pKC30 with ligation.

One of the plasmids obtained after transformation of strain TGE900, pTG906, is treated so as to remove the PvuII-SalI segment. For this purpose, pTG906 is treated successively with SalI, S1 nuclease, PvuII and the ligase. pTG907 is thereby obtained.

Preparation of M13 TG910 (FIG. 11)

The λ cIIrbs "ribosome binding region" (which likewise originates from phage λ) is then inserted in the form of an AvaI-TaqI fragment into the beginning of the lacZ' gene (α fragment of β-galactosidase), which has been cloned in the phage M13 known as M13tg110. This strategy enables a simple functional test to be carried out for rbs, i.e., the production of the lacZ' protein, and consequently allow blue plaques to be obtained in the presence of IPTG and Xgal. This also permits rapid sequencing of the construction using the so-called dideoxy method.

After selection in competent bacteria, a resultant clone M13tg910 is thereby obtained, the overall structure of which is shown at the bottom of the Figure.

Preparation of pTG908 (FIG. 12)

The cIIrbs-lacZ' fragment of phage M13tg910 is transferred to the vector plasmid pTG907 prepared previously.

For this purpose, the EcoRI, BamHI and AvaI sites upstream from cIIrbs are removed and a BglII site is then inserted.

Under these conditions, cIIrbs can be withdrawn in the form of a BglII—BglII fragment and placed in the BamHI site downstream from the P$_L$ promoter and from the λ N gene of pTG907.

Phage M13tg910 is digested with EcoRI and then treated with Ba131, then followed by Klenow polymerase. The fragments obtained are then subjected to the action of the ligase in the presence of non-phosphorylated BqlII adaptor. The ligation mixture obtained is used for transforming competent JM103 cells.

The blue areas are then selected. These clones are then analyzed in order to verify that they contain the BglII site and that they no longer have an EcoRI or BamHI site upstream. Clones such as M13tg912, the structure of which is shown, are thereby obtained.

The treatment with Ba131 produced a 101 bp deletion, eliminating the EcoRI, BamHI and AvaI sites; as well as the lac ATG and lac Shine/Dalgarno sequences. The BglII site introduced is situated approximately 100 bp upstream of the cII ATG and 10 bp downstream of P$_{lac}$.

The BamHI-SphI fragment of pTG907, the BglII/HpaI fragment carrying cIIrbs and lacZ', and the phosphorylated adaptor are prehybridized in a mol ratio of 1:2:1, and then treated with T$_4$ ligase. Aliquots are used for transforming competent cells of strain 6150 at 3° C.

The cells of interest are identified by selecting the transformants with a $^{32}$P-labeled cIIrbs/lacZ' fragment, and the construction obtained is confirmed by an enzyme restriction study.

In order to have an initial indication that the different elements of the expression system are behaving as desired, the plasmid obtained, pTG908, is transferred into an N6437 host strain which possesses both c1857 and the ω fragment of β-galactosidase, which complements the α fragment which is encoded by the plasmid.

The transformants obtained, placed on a dish containing IPTG+Xgal, are colorless at 28° C. and then turn blue after about 30 minutes when they are transferred to 42° C.

Before being used for cloning hirudin, this vector was adapted to clone human interferon-Γ, IFN-Γ, and in fact, for cloning hirudin the nature of the cloned intermediate protein is of no importance, but the vectors were produced according to the scheme below.

Analysis of the IFN-Γ nucleotide sequence for the restriction sites reveals an EcoRII site 8 bp downstream of the starting point of the mature protein and an Sau3A site 285 bp downstream of the stop codon, and this enables virtually the entire sequence coding for the mature protein to be isolated on an EcoRII-Sau3A fragment. The IFN-Γ clone obtained from a library is referred to as pTG11.

Construction of pTG909 (FIG. 13)

A synthetic adaptor molecule is first used, which allows:

a) joining to be accomplished between the EcoRII and NdeI ends, b) the 8 bp, missing with respect to the sequence which codes for mature IFN-Γ, to be introduced, and c) the cIIrbs ATG starting codon to be reconstituted, so that the sequence which codes for the mature IFN-Γ protein is translated without fused amino acids, with the exception of the F-met initiator.

This adaptor is chemically synthesized and its structure is shown in the Figure.

pTG11 is digested with EcoRII and Sau3A, and pTG908 with NdeI and BamHI.

The appropriate fragments are purified on gel, mixed with an equimolar amount of the adaptor, prehybridized and ligated. The mixture is used for transforming competent TGE900 cells, and the transformants are selected by hybridizing a nick-translated, $^{32}$P-labeled pTG11 PstI insert with the transformants.

13 clones are selected and monitored by mapping, and one of these, pTG909, is verified by sequencing.

Construction of the vector pTG941 (FIG. 14)

pTG909 contains 2 NdeI sites, one at the starting codon of IFN-Γ and the other 22 bp downstream from the IFN-Γ sequence.

The region between these sites, which is the region which codes for the first 7 amino acids of IFN-Γ, is removed by treatment with NdeI, and replaced by a synthetic oligonucleotide which is shown in the Figure.

This reaction destroys the NdeI site downstream and reconstitutes the NdeI site upstream, while introducing a BamHI site which is unique. The vector pTG941 is thereby obtained.

Construction of pTG951 (FIG. 15)

FIG. 15 shows schematically the construction of pTG951, which is derived from pTG941, in which the fragment containing the cIIrbs has been replaced by a synthetic sequence based on the sequence of the translation initiation region of the *E. coli* lac operon, designated *E. coli* lac operon rbs. This synthetic oligonucleotide is inserted at the HgaI site between the single NdeI site of the starting codon of the sequence which codes for IFN-Γ the ClaI site which is inserted in the N gene.

As a result, upon treatment with NdeI and ClaI, plasmid pTG951 now only contains a truncated N gene (a stop codon in phase with the translation of the N gene is situated immediately upstream from the new rbs site) and is devoid of the transcription terminators tL1 and tR1 present in pTG909 and pTG941.

The principal results are recorded in the Table below

Expression of hirudin activity by pTG720

*E. coli* TG900 cells containing plasmid pTG720 are grown on LB medium plus 50 μg/ml of ampicillin at 30° C. to an optical density at 600 of 0.3.

The cell cultures are then transferred at 37° C. to induce transcription from the $P_L$ promoter.

1 ml aliquots are withdrawn hourly and the density at 600 nm is measured; then the cells are collected by centrifugation.

| NAME | PROMOTER | RBS | RBS SEQUENCE AND JUNCTION WITH THE SEQUENCE | | | | | | |
|---|---|---|---|---|---|---|---|---|---|
| | | | fmet | cys | tyr | cys | gln | asp | pro |
| PTG909 | PL | cII | TAAGGAAGTACTTACATATG | TGT | TAC | TGC | CAG | GAC | CCA |
| | | | fmet | cys | tyr | cys | gln | asp | pro |
| pTG941 | PL | cII | TAAGGAAGTACTTACATATG | TGC | TAC | TGT | CAG | GAT | CCC |
| | | | fmet | cys | tyr | cys | gln | asp | pro |
| pTG951 | PL | SYNTH (lac) | CACAGGAACAGAGATCTATG ------ BglII | TGC | TAC | TGT | CPG | GAT | CCC |

The examples below are intended to illustrate the preparation of the variant HV2, modified at its N-terminal In the attached figures:

FIG. 16 shows a curve of the hirudin activity induced in an *E. coli* TG900 culture containing pTG720; and FIG. 17 shows a spectrum of analysis of the $^{35}$S-labeled proteins from extracts of *E. coli* TG900 containing pTG720.

Preparation of modified HV2

The construction of plasmid pTG720 expressing hirudin according to the invention is obtained according to the same process as plasmid pTG718 described above, starting with pTG717 and pTG927.

The NdeI-PvuII fragment of pTG927 is assembled with the HinfI-AhaIII fragment of pTG717 by way of adaptor oligonucleotides, described below, in order to reconstitute the ile-thr sequence at the N-terminal end of the hirudin.

The centrifugation pellet is resuspended in 200 μl of TGE (25 mM Tris HCl, pH 8.0, 50 mM glucose, 10 mM EDA) and the cells are lysed by sonication.

After clarification, the supernatant is collected and the antithrombin activity is measured, either by the coagulation test or by colorimetric assay of the inhibition of cleavage of the substrate, tosylglycylprolyl-arginine 4-nitroanilide acetate (Chromozym TH, Boehringer Mannheim GmbH), by a standard solution of thrombin.

The reaction is performed in a reaction volume of 1 ml, using 13 μM substrate in a buffer composed of 100 mM Tris HCl, pH 8.0, 0.15M KCl and 0.1% of polyethylenes glycol 6000.

The reaction with 0.25 U of thrombin is followed or 2 minutes using a spectrophotometer at 405 nm, and the rate of reaction is measured from the slope of the increase in optical density.

Standard hirudin or unknown extracts are added to this thrombin reaction mixture to determine the extent of inhibition or antithrombin activity.

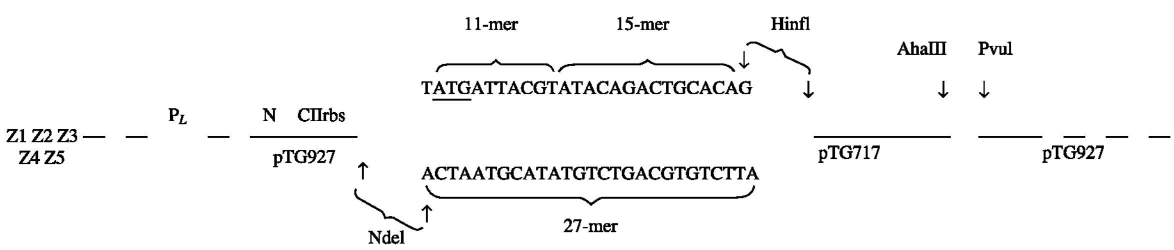

The ligation mixture is used for transforming *E. coli* TG900, and the transformants containing plasmids are selected on an agar-L plate containing 100 ug/ml of ampicillin. The constructions which contain the hirudin sequence are identified by hybridizing the colonies, using a labeled pTG717 insert as probe.

The DNA sequence of the final plasmid is monitored by direct sequencing of the DNA in the expression plasmid.

FIG. 16, attached hereto, shows the effect of induction of antithrombin activity in a culture of cells containing pTG720, expressed as antithrombin units for an optical density of 600 per liter of culture, the induction taking place over a period of 6 hours.

The broken line shows the growth curve of the *E. coli* cells measured at an optical density of 600 during the same period.

As a result of the induction, activity of the hirudin type, showing a significant level, is observed.

Control lysates of the cultures containing the plasmid without the hirudin sequence show no activity.

When these bacterial lysates are heated to 70° C. for 15 minutes after acidification to pH 2.8 with HCl, a considerable amount of protein is denatured and precipitated. When the latter is removed by centrifugation from the cooled extract, and the supernatant is neutralized by adding a Tris HCl buffer (final concentration 100 mM, pH 8.0), at least 100%, and frequently more, of the starting activity reappears in the supernatant.

In a typical experiment, 130% of the starting activity reappears in the supernatant.

No residual activity is found in the precipitated material in the pellet.

When a bacterial extract, heated and acidified after cooling, centrifugation and neutralization (200 μl containing 5 ATU of hirudin), is incubated for 15 minutes at 37° C. with 100 μl of a 50% strength slurry of thrombin covalently coupled to a Sepharose resin (prepared by standard procedures) and when the Sepharose-thrombin is removed by centrifugation, no activity of the hirudin type can be found in the supernatant.

Thus, the hirudin produced by pTG720 has the same general properties as that of the native molecule and as that which is obtained by pTG717 and pTG718.

The polypeptides specifically induced in the pTG720 culture, after labeling with [$^{35}$S]methionine, resolution by electrophoresis on polyacrylamide gel and visualization by fluorography, are shown in FIG. 2. A series of low molecular weight (5 to 10,000 daltons) polypeptides are more especially induced.

Figure 17:
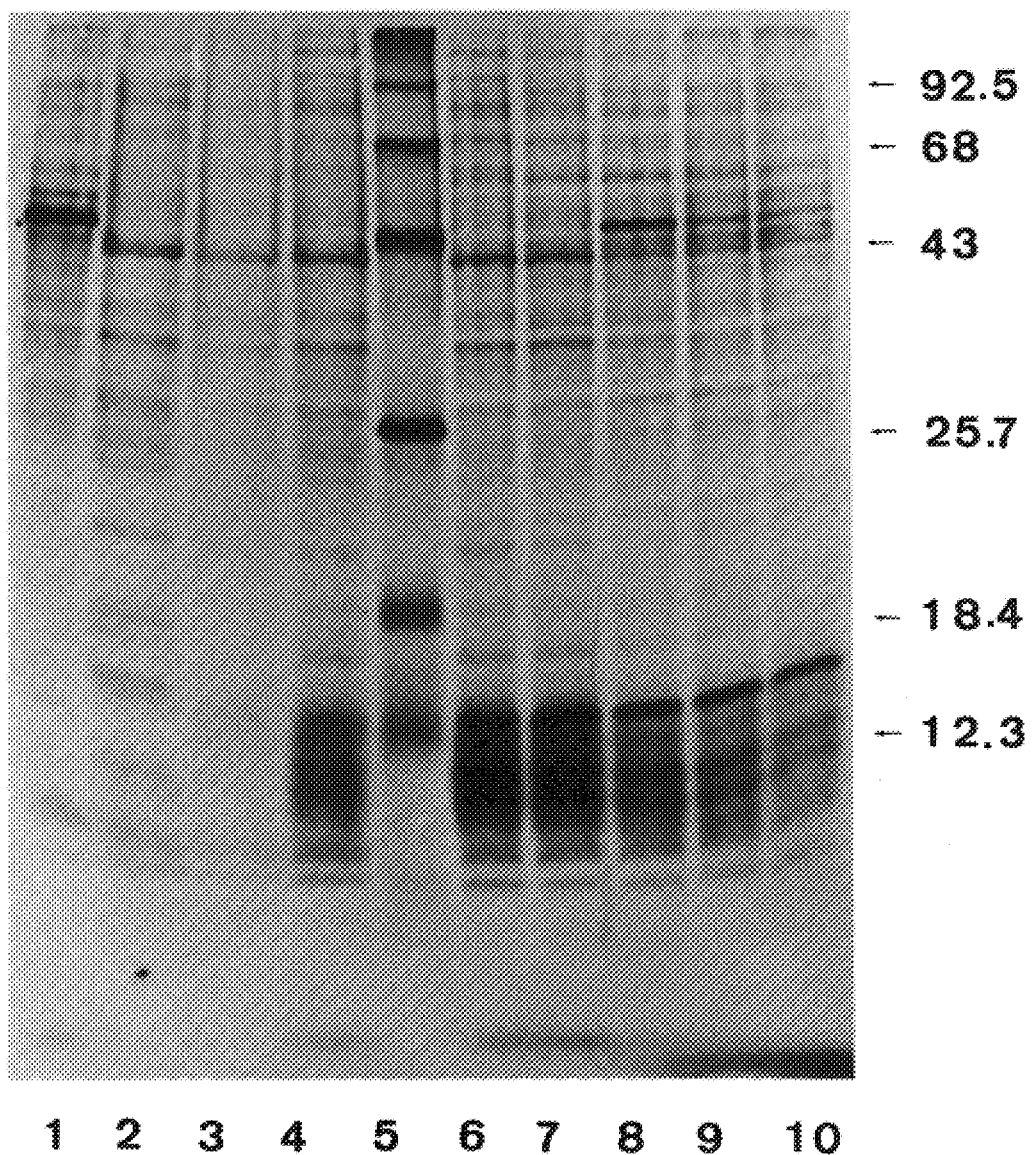
FIG. 17 shows a spectrum of analysis of the $^{35}$S-labeled proteins from extracts of *E. coli* TG900 containing pTG720.

In FIG. 17, lane 1 shows the non-induced cells, lane 2 the induction at 0 hour, lane 3, 1 hour's induction, lane 4, 2 hours' induction, lane 5: molecular weight markers, lane 6, 3 hours' induction, lane 7, 4 hours' induction, lane 8, 5 hours' induction, lane 9, 6 hours' induction, lane 10, 7 hours' induction.

The examples which follow are intended to illustrate the preparation of hirudin HV1.

Study of the HV1 gene and strategy of synthesis

The strategy of synthesis for preparing the gene for hirudin HV1 comprises various stages.

Figure 19:
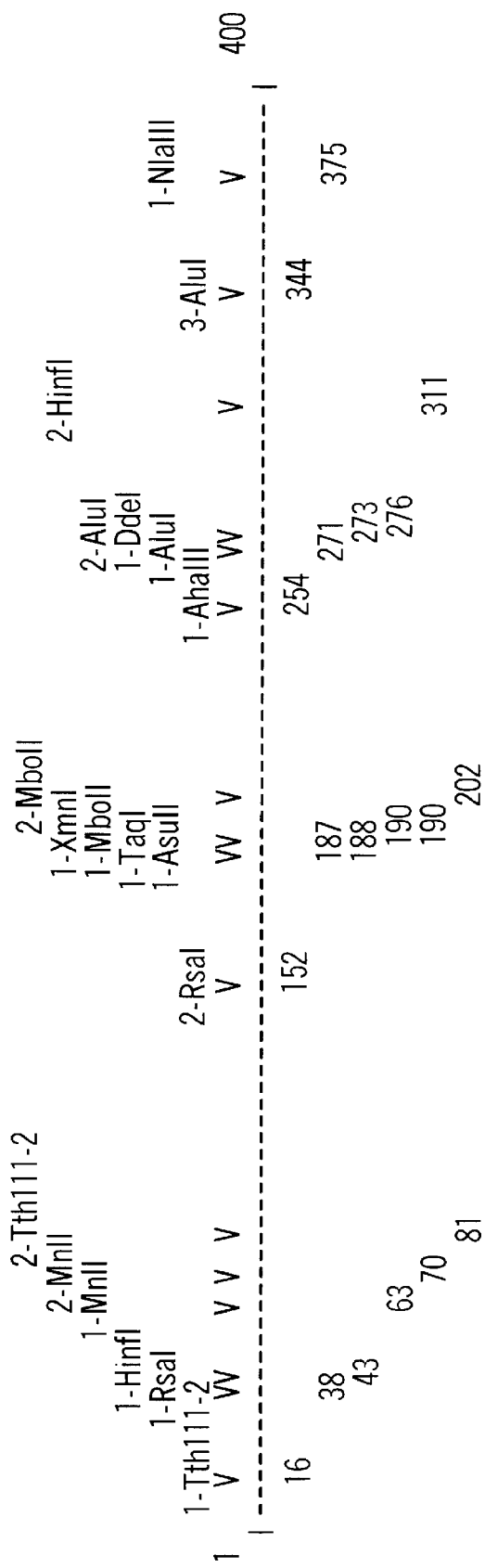
FIG. 19 shows the single TaqI site in the cDNA of HV2 cloned in pTG717 which is centered on amino acid 56.

First, since there is no difference in amino acids between HV1 and HV2 after amino acid 53, as is seen in FIG. 18, and since there is a single TaqI site in the cDNA of HV2 cloned in pTG717 which is centered on amino acid 56 (FIG. 19), the DNA sequence of the variant HV1 after amino acid 56 can be provided by the TaqI-PstI fragment of pTG717.

For this reason, only the DNA coding for the first 56 amino acids of HV1 have to be chemically synthesized.

Figure 20:
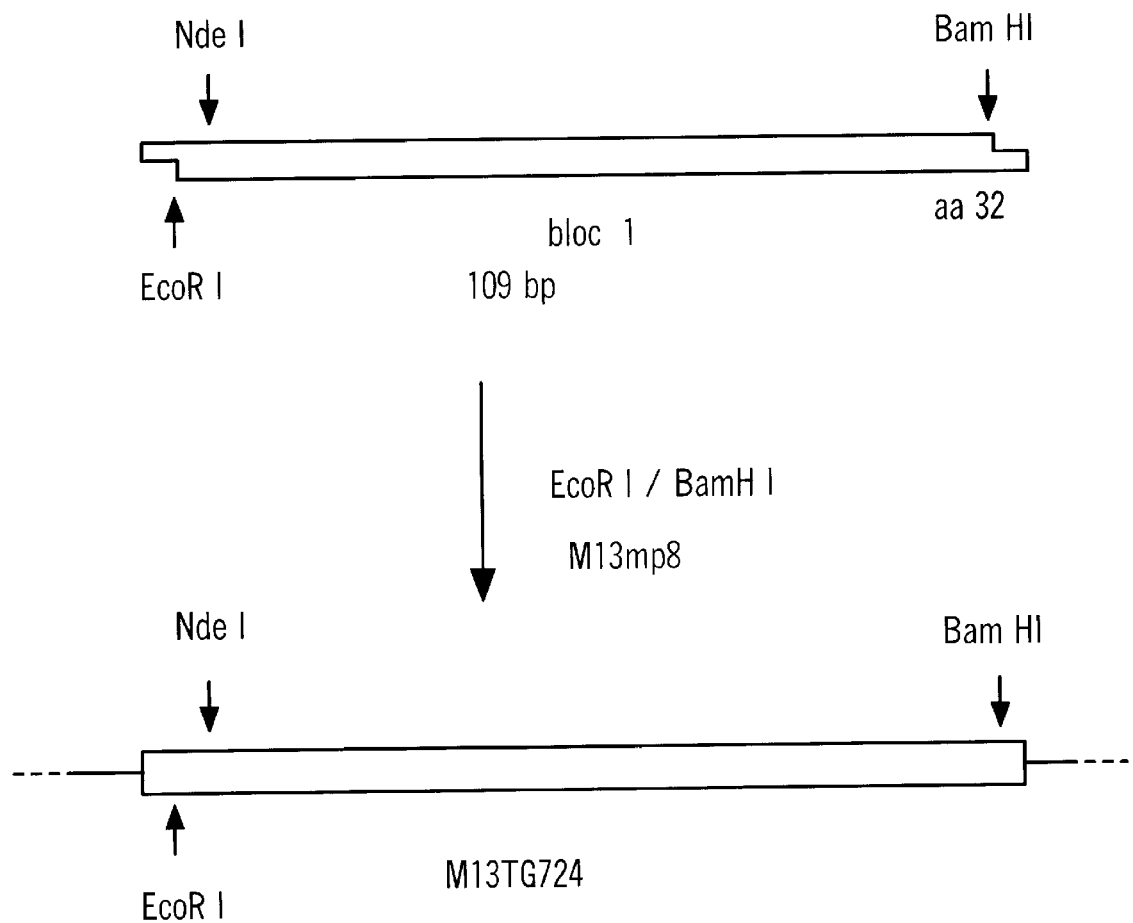
FIG. 20 shows block 1 in the synthesis of the first 56 amino acids of HV1.

This DNA was synthesized in two separate blocks. The first, shown in FIG. 20, begins with an EcoRI cohesive site which is primarily intended for cloning, immediately followed by an NdeI site which incorporates the ATG initiation codon before the sequence which codes for HV1. The complete gene can be withdrawn, using the NdeI site at the 5' end, for insertion in an expression vector in E. coli. This portion is followed by a DNA extension coding for amino acids 1 to 32 of HV1, and can be terminated by a BamHI cohesive end, since amino acids 31 and 32 are gly and ser, and can be encoded by a BamHI site, as shown:

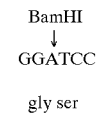

This synthetic DNA portion which possesses 109 bp, is assembled by condensing its constituent oligonucleotides, and is then placed by ligation in phage M13mp8 cut with EcoRI/BamHI in order to lead to the construction M13TG724. Since the synthetic DNA is present in the poly-linker region of phage M13, it can be immediately sequenced to verify that this first synthetic block is correctly assembled.

Figure 21:
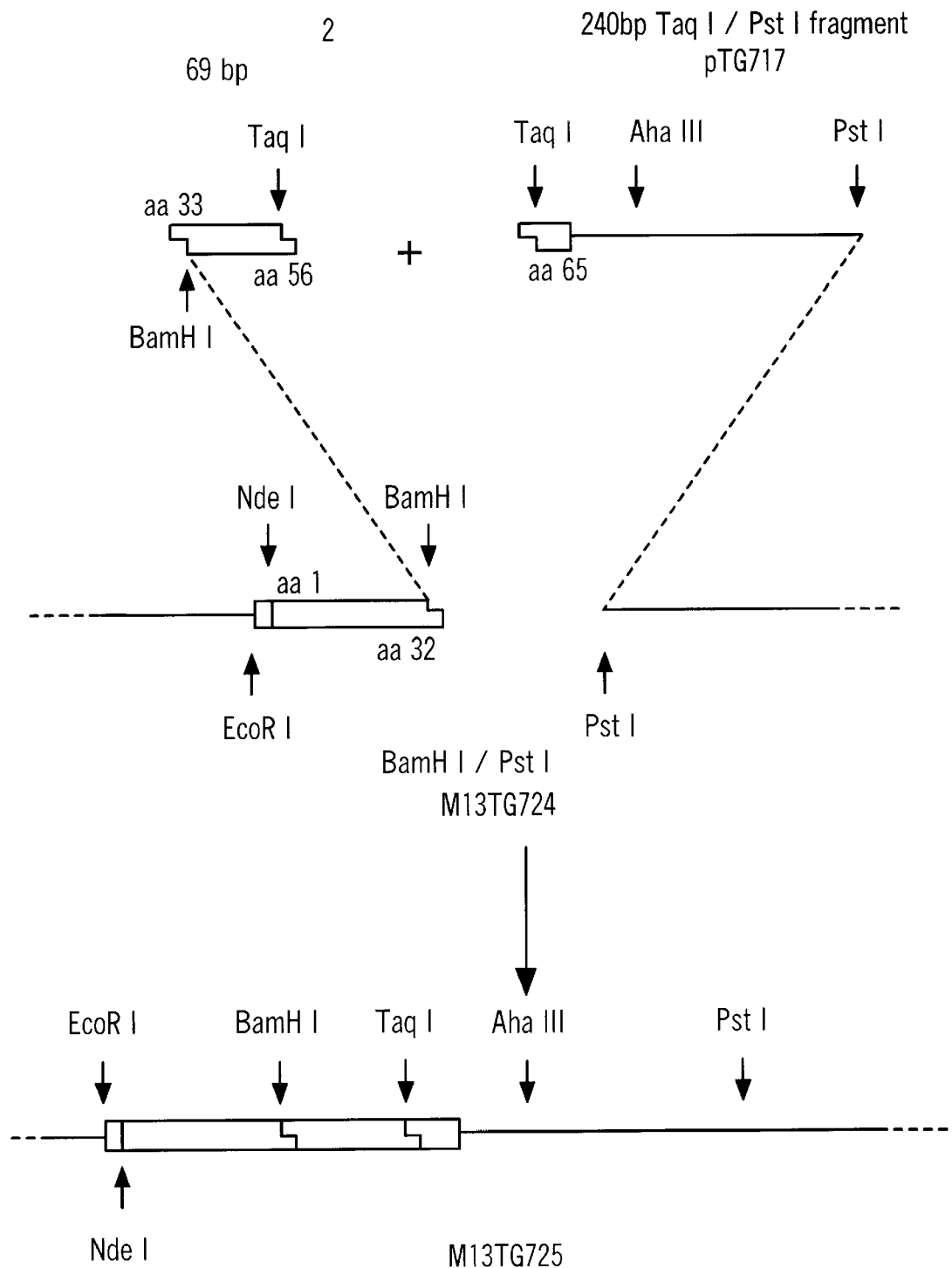
FIG. 21 shows the synthesis of block 2 of the first 56 amino acids of HV1.

The second synthetic block corresponds to amino acids 33 to 56, and is limited at one end by a BamHI cohesive site and at the other end by a TaqI site (FIG. 21). This 69 bp synthetic block is again assembled from its constituent oligonucleotides, and then incorporated with the TaqI-PstI fragment originating from pTG717 into M13TG724 cut with BamHI/PstI, as shown in FIG. 21. This leads to a phage M13TG725 which contains the sequence coding for the complete HV1. As above, the correct assembly of this construction can be immediately verified by sequencing.

Figure 22:
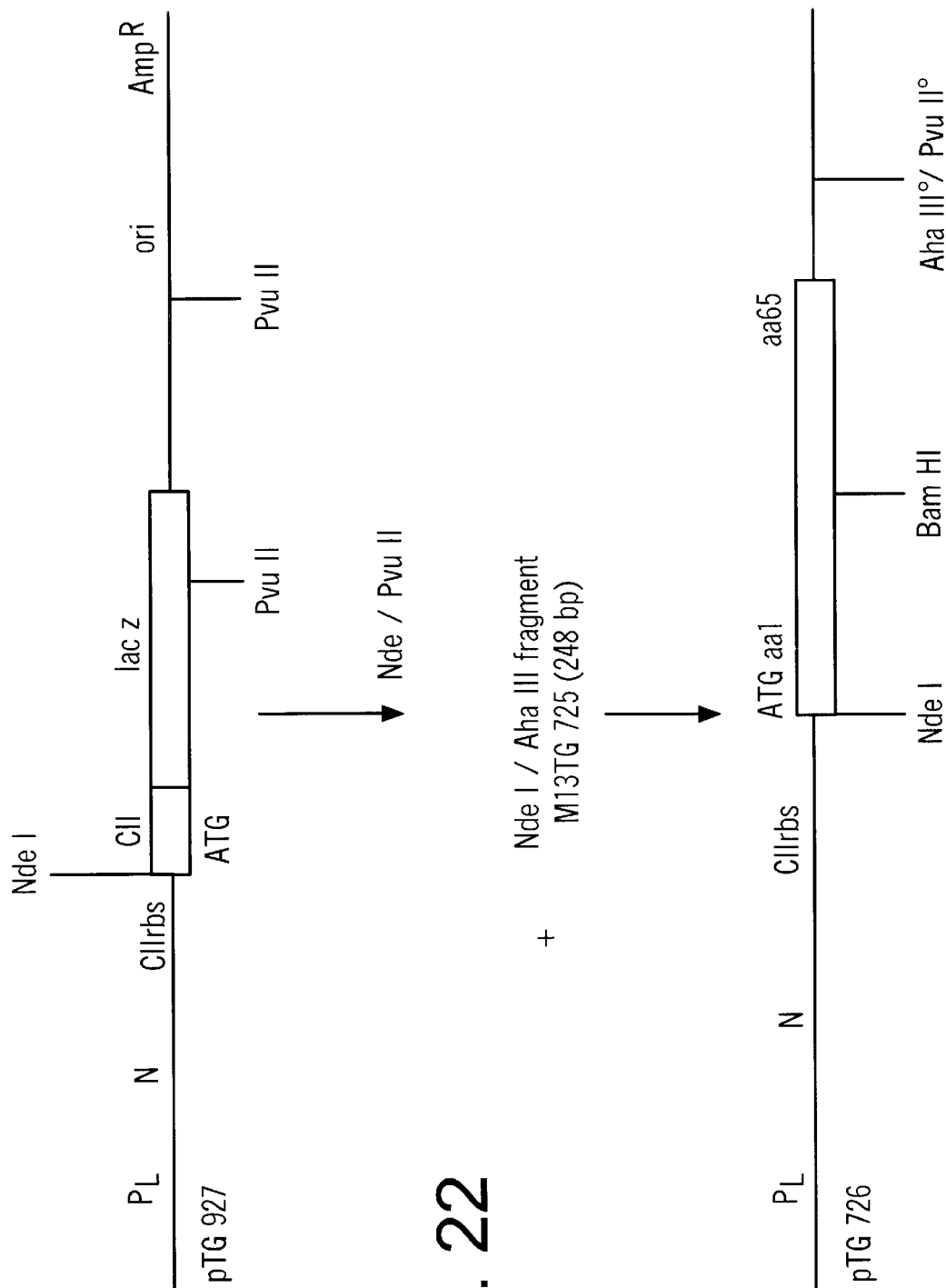
FIG. 22 shows pTG726.

The following stage comprises the transfer of the NdeI-AhaIII fragment, which begins with the ATG of the hirudin sequence and terminates in a non-translated region at the 3' end, into plasmid pTG927 cut with NdeI/PvuII. This expression vector is identical to that which was used for constructing the hirudin HV2 expression vector pTG720, and its structure and construction have already been described. The final expression vector coding for the variant HV1 is known as pTG726, and is shown in FIG. 22.

The exact sequence of the oligonucleotides used for constructing these two blocks is shown in FIG. 23. Block 1 extends from the EcoRI site to the BamHI site, and is composed of 8 oligonucleotides having sizes which range from 22 to 32 bases. Block 2 extends between the BamHI site and the TaqI site, and is composed of 6 oligonucleotides having sizes ranging from 19 and 30 bases.

The oligonucleotides are synthesized by a manual phosphotriester procedure on a silica support (reference 31) and are purified using HPLC techniques or elution from polyacrylamide gel.

The exact sequence of the oligonucleotides used for the synthetic portion of the gene is chosen having with the following parameters in mind:

a) the choice of codons, where possible, is that for the genes which are expressed at very high levels in E. coli; this choice is made using published data (ref. 32, 33);

b) computer analysis of each of the oligonucleotides, individually and then in complete sequence, so as to eliminate structures which can form "hairpins";

c) the choice of N-terminal the end of the hirudin molecule corresponds to the preferred use of certain codons to obtain the bases in certain positions in this region, where it has been shown that these bases were important for a high level of expression of foreign proteins in E. coli.

Assembly of the synthetic gene First synthetic block

The oligonucleotides forming this block, 1–8 (FIG. 23), are phosphorylated at their 5' end with polynucleotide kinase under standard conditions, except for the two end oligonucleotides 1 and 8. This is intended to avoid the formation of dimer or polymer of the synthetic block in the following ligation stages. 500 picomoles of each of the oligonucleotides are subjected to the action of kinase, using 2 units of polynucleotide kinase in a final 25 µl volume of 60 mM Tris HCl, pH 7.5, 10 mM $MgCl_2$, 8 mM dithiothreitol, also containing 3.3 pmol of $[\Gamma-^{32}P]ATP$, the specific activity of which is 5000 Ci/mmol. After incubation for 15 minutes at 37° C., the oligonucleotides are then completely phosphorylated by adding 5 mmol of cold ATP.

After incubation for a further 15 minutes at 37° C., the oligonucleotides are purified by electrophoresis on 20% polyacrylamide gel, performed under denaturing conditions. The labeled oligonucleotides are detected by autoradiography, the appropriate regions of the gel are excised and the oligonucleotides are eluted with water during incubation overnight at 37° C.

The oligonucleotides are then charged onto columns of DEAE-cellulose, eluted with a 1M triethylammonium bicarbonate buffer, pH 8, and lyophilized.

For oligonucleotides 1 and 8, which were not subjected to kinase and not labeled, gel purification is carried out as above but the oligonucleotides are detected by UV absorption.

The complementary fragments (1+5, 2+6, and the like) are mixed, using equivalent amounts 100 picomoles of each of the oligonucleotides in a final 50 µl volume of 66 mM Tris HCl, pH 7.5, 6 mM $MgCl_2$, 100 mM NaCl, 0.5 mM spermidine and 8 mM dithiothreitol. These mixtures are heated to 100° C. and cooled slowly to 37° C. for 2 hours. The solutions are mixed to give hybrids with 4 oligonucleotides in 100 µl. The mixtures are finally united and the 8 oligonucleotides are left to form pairs overnight at 37° C. in a final volume of 200 µl. 0.005 picomoles of the paired oligonucleotides are ligated with 25 ng of M13mp9, digested with BamHI/EcoRI and purified on gel, in a final 20 µl volume of a ligation mixture containing 66 mM Tris pH 7.5, 6.6 mM $MgCl_2$, 10 mM dithiothreitol, and 0.5 mM ATP.

The ligation is continued at 15° C. for 24 hours, followed by ligation for 24 hours at 4° C. The ligation mixture is then used for transforming E. coli JM103. From many colorless plaques obtained by transformation, 8 candidates are selected, single-stranded DNA is prepared from the phages and this is subjected to direct DNA sequencing by the dideoxy chain termination method (reference 34). From these candidates, two are found to contain the correct assembly of oligonucleotides corresponding to block 1 of FIG. 23, and one of these is designated as M13TG724 and used in the following stage.

Second synthetic block and assembly of the whole gene

To assemble the second synthetic block, the strategy used was essentially the same as that described above, with the exception that the oligonucleotide constituents are not pre-purified before the pairing stage, but instead are subjected to kinase (except for the terminal oligonucleotides 9 and 14; see FIG. 23) and then directly paired. The pairing conditions are the same as those described above, with 100 picomoles of each of the oligonucleotides in a final volume of 150 ul.

After the pairing stage, the mixture is charged on a 2% agarose gel (low melting point agarose) and then subjected to electrophoresis. The oligonucleotides are detected by staining with ethidium bromide and the bands corresponding to the assembled block (69 bp) are cut from the gel and eluted by standard procedures.

The second synthetic block (2 ng) is then mixed with 50 ng of phage M13TG724, cut by PstI/BamHI and purified on gel, and 2 ng of a TaqI-PstI fragment of pTG717 purified on gel. The combination of these elements is assembled in a 20 µl volume of 66 mM Tris HCl, pH 7.5, 6.6 mM Mg $Cl_2$, and heated to 65° C. for 5 minutes, and there are added DTT to a concentration of 10 mM, ATP to a concentration of 0.5 mM and 5 units of $T_4$ ligase. The ligation is continued for 16 hours at 15° C. and the ligation mixture is then used for transforming E. coli JM103.

From the colorless plaques among the transformants, 12 are chosen, which are selected for preparing a single-stranded phage for direct sequencing. Furthermore, the phage is also prepared in double-stranded form (reference 35) to study the existence of a single BamHI site which has to be present in the correctly assembled recombinates. The majority of these clones contain both the BamHI site and the DNA sequence corresponding to the correct assembly of the whole gene coding for HV1. One of these, designated M13TG725, is chosen.

Transfer of the HV1 gene to the expression vector

The final stage for creating the vector plasmid capable of expressing the HV1 protein consists of transferring the 248 bp NdeI-AhaIII segment of M13TG725 into pTG927 cut by NdeI/PvuII (FIG. 22). However, since the replicative form of the phage with this type of digestion leads to a second M13 fragment, which is practically the same size but which clones more efficiently in the expression vector than the desired fragment, it is necessary first to prepare an AvaII-BglII fragment (1.71 kb) which contains the whole of the hirudin HV1 sequence, and then to digest it with NdeI/AhaIII. This digestion product, without further purification, is ligated in the expression vector pTG927 after cutting with NdeI/PvuII. Among the transformants of E. coli TGE900, the correct construction pTG726 is identified by the presence of a single BamHI site derived from the sequence of the HV1 gene, and then by direct DNA sequence analysis.

Expression of the biological activity of hirudin HV1 with pTG726

The expression vector pTG726 contains a temperature inducible promoter, the $P_L$ promoter, the major leftward promoter of bacteriophage λ. Since this promoter is blocked by a temperature sensitive repressor encoded by the host, the hirudin HV1 gene is not transcribed during growth at 30° C. However, when the temperature is raised above 37° C., the transcription of this gene is induced.

Figure 24:
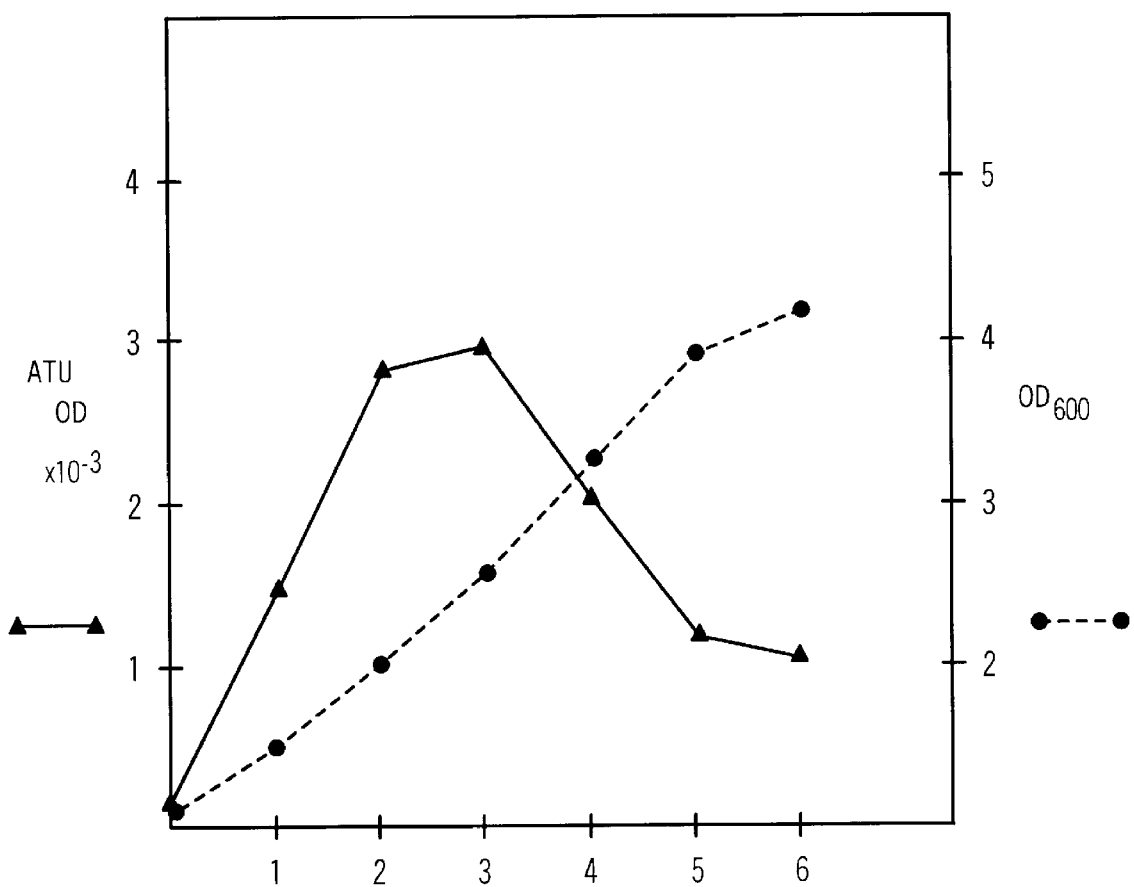
FIG. 24 is a graph showing the induction of antithrombin activity in an *E. coli* pTG726 culture grown at 30° C. to an optical density of 0.3 at 600 nm, followed by induction at 37° C.

FIG. 24 shows the growth curve and the curve for induction of antithrombin activity in an E. coli pTG726 culture grown at 30° C. to an optical density of 0.3 at 600 nm, followed by induction at 37° C.

The hirudin activity is measured by the capacity of the sonicated extracts of the bacterial cells to inhibit bovine thrombin activity with respect to its capacity to cleave chromogenic substrates.

It is clear that significant amounts of hirudin are induced in the pTG726 cultures. Approximately 3 to 4,000 antithrombin units/OD/liter of culture, but this activity declines rapidly as time proceeds. This effect is readily reproducible, with a peak of activity 3 hours after induction, followed by a stage of decline.

Figure 25:
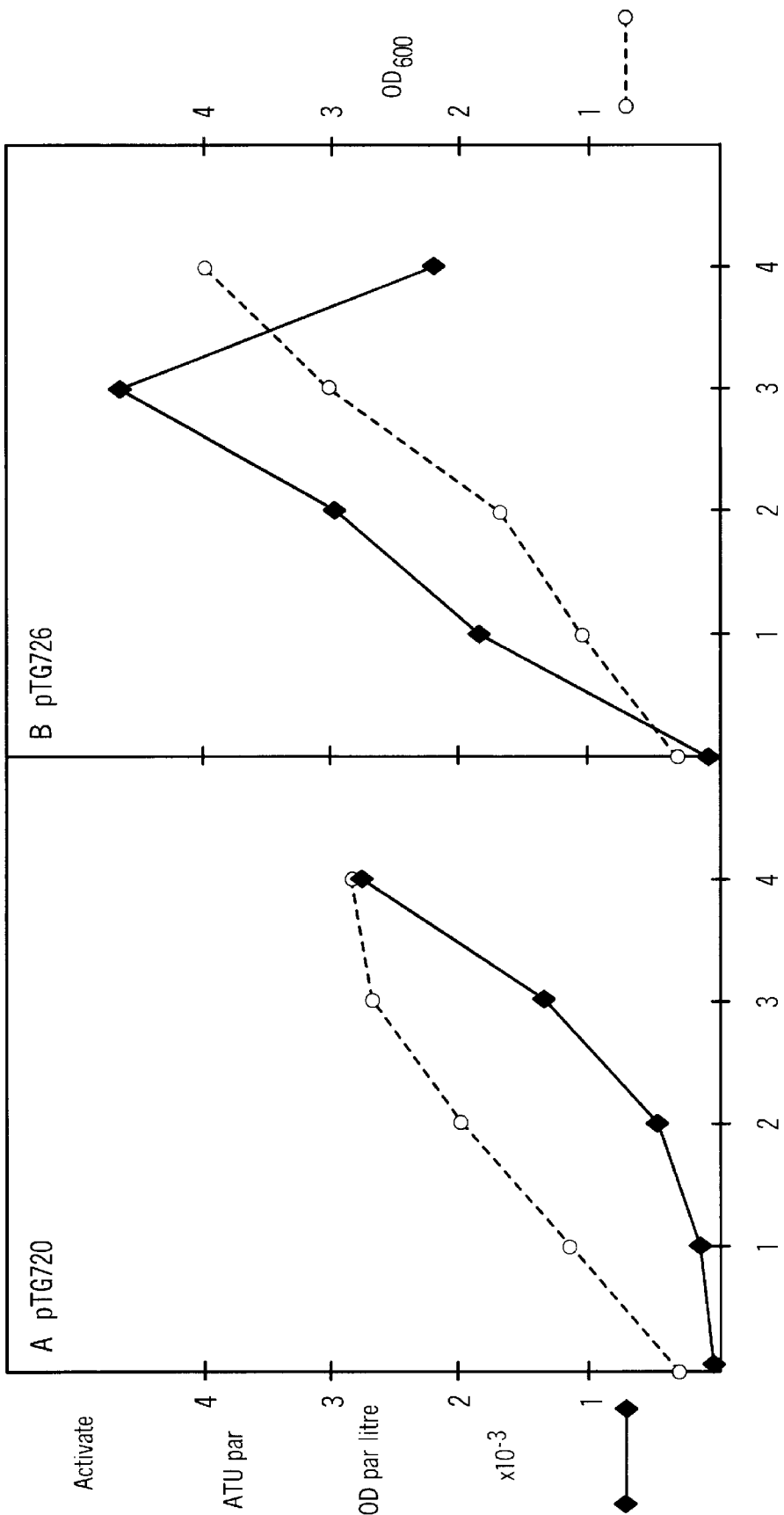
FIG. 25 is a graph showing the induction curve for pTG720 culture (FIG. 25A) and pTG726 culture (FIG. 25B).
Figure 26:
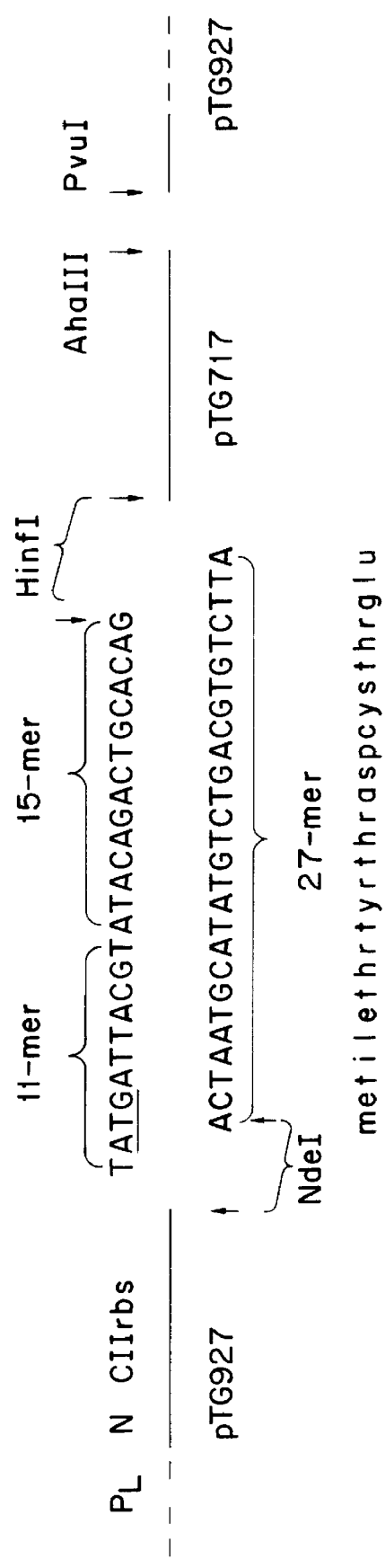
FIG. 26 shows the NdeI-PvuII fragment of pTG927 assembled with the HinfI-AhaIII fragment of pTG717 using adaptor oligonucleotides.

The nature of this induction curve is very characteristic and reproducible, and differs significantly from those which have been observed previously with the expression vector pTG720 which, on induction, expresses the hirudin variant HV2. This variant is induced much more slowly (FIG. 25A) with a latency period of approximately 2 hours, the activity increasing to reach virtually the same level as that of pTG726 (FIG. 25B) but then remaining constant without any indication of a decline. Since the two hirudin variants were produced using exactly the same expression vector in exactly the same E. coli TGE900 host cell, this difference in induction and stability must definitely be connected with differences in the primary structures between HV1 and HV2. This may, furthermore, reflect a difference in the resistances to proteolytic digestion between the two variants, and may be an indication of different biological activities or of different biological roles for the two variants. Such differences in stability and other biological properties can possibly be turned to account in the use of these hirudins.

The difference in the expression of HV1 and HV2 in E. coli can also be observed by pulse-labeling analysis of E. coli TGE900 cells transformed by two different expression vectors. Since the two hirudin variants are very rich in cysteine (approximately 10% of the molecule), and since this amino acid is rather uncommon in E. coli proteins, [$^{35}$S]cysteine is very useful as a radioactive marker for the expression of hirudin. E. coli cells transformed by pTG726 are grown at 30° C. to an optical density of 0.3 determined in LB+ampicillin (100 μg/ml), and then induced to express the variant HV1 by increasing the temperature to 37° C.

At regular hourly intervals, a 200 μl aliquot of the culture is withdrawn and 70 μCi of [$^{35}$S]cysteine (specific activity 1000 Ci/mmol) are added for a labeling period of 2 minutes. A large excess, approximately 2 ml, of cold phosphate buffered saline is then added, the cells are collected by centrifugation and the labeled proteins in the whole cells are analyzed by boiling the pellet for 5 minutes in 40 μl of a loading buffer for an SDS gel (50 mM Tris HCl, pH 6.8, 1.3% SDS, 5% glycerol, 2.5% β-mercaptoethanol, 0.004% bromophenol blue) and charge (sic) of 5 μl on a 15% SDS-polyacrylamide gel (procedure of laemli-reference 36). After electrophoresis, the gel is subjected to fluorography followed by auto-radiography.

The results show the induction of a series of bands in the region of 6,000 to 12,000 daltons, corresponding to hirudin. These bands are only weakly labeled with the E. coli/pTG726 extracts (variant HV1), whereas they are very strongly labeled with the E. coli/pTG720 extracts.

This very distinct difference in the pattern of labeling appears in spite of the fact that the two cultures show approximately the same level of antithrombin activity.

Other properties of the hirudin recombinant HV1

One of the characteristics of natural hirudin, and also of the variant HV2 prepared by E. coli, is its resistance to heat treatment under conditions of quite low pH. This is also true for the variant HV1 prepared from E. coli. A culture, induced for 3 hours, of E. coli cells transformed by pTG726 is collected by centrifugation and resuspended in ⅕ of the culture volume of TGE (50 mM Tris HCl, pH 8.0, 50 mM glucose, 10 mM EDTA) and the cells are shattered by sonication. The cell debris is removed by centrifugation and a portion of the supernatant is used directly for determination of the antithrombin activity.

Another portion, is adjusted to pH 2.8 with dilute HCl, and then heated to 70° C. for 15 minutes. The mixture is then cooled in ice for 30 minutes and the denatured insoluble proteins are removed by centrifugation. The supernatant is neutralized by adding dilute NaOH and the antithrombin activity is then measured. After the small modifications in volume due to the acidification and neutralization are taken into account, it can be calculated that 100% of the original activity survives this acid/heat treatment. For this reason, the variant HV1 is identical to natural hirudin and to the variant HV2.

The hirudin HV2 activity can also be completely removed from a bacterial extract by using thrombin linked covalently to Sepharose beads. An E. coli/pTG726 extract treated with acid and heat and then neutralized, and containing 7.7 units of antithrombin activity in 200 μl, is incubated with 50 μl of a 50% strength suspension of thrombin-Sepharose for 15 minutes at 37° C. The beads of thrombin-Sepharose are removed by centrifugation and the supernatant is tested for its antithrombin activity. More than 95% of the original antithrombin activity is removed by Sepharose-thrombin treatment. The variant HV1 produced by the E. coli cells is consequently capable of binding to thrombin bound to Sepharose beads.

The following strains were filed on Mar. 26th 1985 in the Collection Nationale de Cultures de Microorganisms (CNCM) (National Collection of Microorganism Cultures) -28 rue du Docteur-Roux-75724 PARIS CEDEX 15:

E. ColiTGE900 transformed by pTG718 No. I-427
E. Coli TGE900 transformed by pTG720 No. I-428
E. Coli TGE900 transformed by pTG726 No. I-429

REFERENCES

1. Markwardt, F. (1955) Naturwissenschaften 42, 587.
2. Markwardt, F. (1957) Hoppe-Seylers Z. Physiol. Chem. 308, 147–156.
3. Markwardt, F. and Walsmann, P. (1967) Hoppe-Seylers Z. Physiol. Chem. 348, 1381–1386.
4. de la Llosa, Tertrin, C. and Jutisz, M. (1963) Bull. Soc. Chim. Biol. 45, 63–74.
5. Markwardt, F. (1970) in Methods in Enzymology, eds. Perlman, G. E. and Lorand, L., Academic Press., vol. 19, pp. 924–932.
6. Bagdy, D., Barabas, E. and Graf, L. (1973) Thrombosis Research 2, 229–238.
7. Graf, L., Patthy, A., Barabas, E. B., and Bagdy, D. (1973) Biochim. Biophys. Acta 310, 416–417.
8. Petersen, T. E., Roberts, H. R., Sottrup-Jensen, L., Magnusson, S. and Bagdy, D. (1976) Protides Biol. Fluids, Proc. Colloq. vol. 23, pp. 145–149.
9. Dodt, J., Müller, H.-P., Seemüller, U., and CHang, J.-Y. (1984) Febs Lett. 165, 180–183.
10. Krajewski, T., and Blomback, B. (1968) Acta. Chem. Scand. 22, 1339–1346.
11. Chang, J.-Y. (1983) Febs. Lett. 164, 307–313.
12. Baskova, I. P., Cherkesova, D. U., MosoLov, V. V., Maviova, E. L., and Belyanova, L. A. (1980) Biokhimiya 45, 463–467.
13. Baskova, I. P., Cherkesova, D. U., and Mosolov, V. V. (1983) Thrombosis Research 30, 459–467.
14. Markwardt, F., Hauptmann, J., Nowak, G., Klessen, Ch., and Walsmann, P. (1982) Thromb. Hemostasis (Stuttgart) 47, 226–229.
15. Walsmann, P. and Markwardt, F. (1981) Die Pharmazie 10, 653–660.
16. Kloss, Th., and Mittmann, U. (1982) Longenbecks Arch. Chirurg. 358, 548.

17. Ishikawa, A., Hafter, R., Seemüller, U., Gokel, J. M., and Graeff, M. (1980) Thrombosis Research 19, 351–358.
18. Nowak, G., and Markwardt, F. (1980) Expt. Path. 18, 438–443.
19. Sutor, A. H., Knop, S., and Adler, D. (1981) in Kontrolle Antithrombotica, 23rd Symp. Blutgerinnung, Hamburg, pp. 117–123.
20. Bagdy, D., Barabas, E., Graf, L., Petersen, T. E. and Magnusson, S. (1976) in Methods in Enzymology part B, vol. 45, pp. 669–678.
21. Walsmann, P. (1981) Pharmazie 36, 860–861.
22. Aviv, H., and Leder, P. (1972) Proc. Natl. Acad. Sci. USA 69, 1408–1412.
23. Jaye, M., De La Salle, H., Schamber, F., Balland, A., Kohli, V., Findeli, A., Tolstoshev, P. and Lecocq, J. P. (1983) Nucleic Acids Res. 11, 2325–2335.
24. Szostak, J. W., Stiles, J. I., Tye, B.-K., Chiu, P., Sherman, F. and Wu, R. (1979) in Methods in Enzymology, vol. 68, pp. 419–428.
25. Kohli, V., Balland, A., Wintzerith, M., Sauerwald, R., Staub, A. and Lecocq, J. P. (1982) Nucl. Acids Res. 10, 7439–7448.
26. Sanger, F., Nicklen, S. and Coulson, A. R. (1977) Proc. Natl. Acad. Sci. USA 74, 5463–5467.
27. Thomas, P. (1980) Proc. Natl. Acad. Sci. USA 77, 5201–5205.
28. Kalckar, H. (1947) J. Biol. Chem. 167, 461.
29. Caen, J., Larrieu, M. J. and Samama, M. (1975) in "L'Hémostase, Méthode d'exploration et diagnostic pratique" 2nd edition, Ed. L'Expansion Scientifique, Paris.
30. Vieira J. and Messing J., Gene 19, 259–268.
31. Kohli, V., Balland A., Wintzerith M., Sauerwald R., Staub A. and Lecocq J-P, (1982) Nucl. Acids Res. 10, 7439–7448.
32. Grantham, R., Gauthier C., Gouy M., Jacobzon E. M. and Mercier R. (1981) Nucl. Acids Res. 9, 143–174.
33. Ikemura T. (1981) J. Molec. Biol. 151, 389–409.
34. Sanger F., Coulson A. R., Barrel B. G., Smith A. J. H. and Roe B. A., J. Mol. Biol. (1980) 161–178.
35. Birnboim H. C. and Doly S., Nucl. Acids Res. (1979) 7, 1513.
36. Laemli U., Nature (1970) 227, 680–685.

What is claim is:

1. A vector for producing a hirudin variant in a transformed host procaryotic cell, said vector comprising a DNA fragment encoding a hirudin variant having an amino acid sequence as follows:

| | | | | | | | | | |
|---|---|---|---|---|---|---|---|---|---|
| Ile | Thr | Tyr | Thr | Asp | Cys | Thr | Glu | Ser | Gly |
| Gln | Asn | Leu | Cys | Leu | Cys | Glu | Gly | Ser | Asn |
| Val | Cys | Gly | Lys | Gly | Asn | Lys | Cys | Ile | Leu |
| Gly | Ser | Asn | Gly | Lys | Gly | Asn | Gln | Cys | Val |
| Thr | Gly | Glu | Gly | Thr | Pro | Asn | Pro | Glu | Ser |
| His | Asn | Asn | Gly | Asp | Phe | Glu | Glu | Ile | Pro |
| Glu | Glu | Tyr | Leu | Gln, | | | | | | said vector being capable of expressing said variant.

2. A vector according to claim 1, having an origin of replication which is of bacterial origin.

3. A vector according to claim 1, which is selected from the group consisting of pTG720, pTG718 and pTG719.

4. A procaryotic cell transformed with a vector according to claim 1.

5. A cell according to claim 4, which is a bacterium.

6. A cell according to claim 5, which is of the *E. coli* species.

7. A process for preparing a hirudin variant having an amino acid sequence starting at the N-terminal end with an Ile residue immediately followed by a Thr residue, which comprises the steps of culturing a procaryotic cell according to claim 4 and recovering from the culture said hirudin variant.

8. A vector according to claim 1, which is pTG726.

* * * * *

UNITED STATES PATENT AND TRADEMARK OFFICE
CERTIFICATE OF CORRECTION

PATENT NO. : 5,824,505                                    Page 1 of 2

DATED:        : October 20, 1998

INVENTOR(S) : Paul TOLSTOSHEV et al.

It is certified that error appears in the above-identified patent and that said Letters Patent is hereby corrected as shown below:

The sheet of drawing consisting of figure 18 should be deleted to appear as per attached figure 18

Signed and Sealed this

Seventh Day of March, 2000

Attest:

Attesting Officer

Q. TODD DICKINSON

Commissioner of Patents and Trademarks

FIG. 18

```
                                    Pst I
                                     ↓  1                                    21
                              a)  ⁻(G)ₙGCA ATC TGC GTG TCT CAA GCA
                              b)      Ala Ile Cys Val Ser Gln Ala
```

```
       22                                                              66
a)   ATT ACT TAC ACT GAT TGT ACA GAA TCG GGT CAA AAT TTG TGC CTC
      1                                                                15
b)   Ile Thr Tyr Thr Asp Cys Thr Glu Ser Gly Gln Asn Leu Cys Leu
      1   2
c)   Val Val ------------------------------------------------------
```

```
      67                                                              111
    TGC GAG GGA AGC AAT GTT TGC GGT AAA GGC AAT AAG TGC ATA TTG
     16                                                               30
    Cys Glu Gly Ser Asn Val Cys Gly Lys Gly Asn Lys Cys Ile Leu
                                     24
    -------------------------------- Gln --------------------
```

```
     112                                                             156
    GGT TCT AAT GGA AAG GGC AAC CAA TGT GTC ACT GGC GAA GGT ACA
     31                                                               45
    Gly Ser Asn Gly Lys Gly Asn Gln Cys Val Thr Gly Glu Gly Thr
             33      35  36
    ------- Asp ---- Glu Lys -------------------------
                                                  Taq I
                                                   ↓
     157                                                             201
    CCG AAC CCT GAA AGC CAT AAT AAC GGC GAT TTC GAA GAA ATT CCA
     46                                                               60
    Pro Asn Pro Glu Ser His Asn Asn Gly Asp Phe Glu Glu Ile Pro
         47      49              53
    --- Lys ---- Gln --------- Asp ------------------------
                                                              Aha III
     202                                                       256 ↓
    GAA GAA TAT TTA CAA TGAAAAATGAAAGAATATCAATCATAGAGAATTTTGATTT
     61               65
    Glu Glu Tyr Leu Gln
```

```
    ------------------
```

```
     257                                                             316
    AAAAACATTTCCATAGCTAAGCTATTTACCAATAAATAAATTAATTTTTTCCATTGAATCT
```

```
     317                                                             376
    CAATCATATTTACTCTCAATCATATTCAGCTATTTACCAATAAATAAATTAATTTTTTCCA
```

```
              Pst I
     377       ↓
    TGA(C)ₙ
```